(12) United States Patent
Chen et al.

(10) Patent No.: US 7,977,499 B2
(45) Date of Patent: Jul. 12, 2011

(54) BIS(FERROCENYLPHOSPHINO) FERROCENE LIGANDS USED IN ASYMMETRIC HYDROGENATION REACTIONS

(75) Inventors: Weiping Chen, Liverpool (GB); Felix Spindler, Starrkirch-Will (CH); Ulrike Nettekoven, Basel (CH); Benoît Pugin, Münchenstein (CH)

(73) Assignee: Solvias AG, Basel (CH)

( * ) Notice: Subject to any disclaimer, the term of this patent is extended or adjusted under 35 U.S.C. 154(b) by 0 days.

(21) Appl. No.: 12/449,638

(22) PCT Filed: Feb. 15, 2008

(86) PCT No.: PCT/EP2008/051836
§ 371 (c)(1),
(2), (4) Date: Dec. 28, 2009

(87) PCT Pub. No.: WO2008/101868
PCT Pub. Date: Aug. 28, 2008

(65) Prior Publication Data
US 2010/0160660 A1    Jun. 24, 2010

(30) Foreign Application Priority Data
Feb. 20, 2007 (CH) ..................... 0282/07

(51) Int. Cl.
*C07F 15/00* (2006.01)
*C07C 57/30* (2006.01)
(52) U.S. Cl. ............... 556/22; 556/14; 562/496
(58) Field of Classification Search ............ 556/14, 556/22; 562/496
See application file for complete search history.

(56) References Cited

U.S. PATENT DOCUMENTS
2007/0232653 A1   10/2007   Bachmann et al.

FOREIGN PATENT DOCUMENTS
| WO | 01/58588 | 8/2001 |
| WO | 2006/075166 | 7/2006 |
| WO | 2006/075177 | 7/2006 |
| WO | 2007/113155 | 10/2007 |

OTHER PUBLICATIONS

International Search Report dated May 21, 2008 in the International (PCT) Application PCT/EP2008/051836 of which the present application is the U.S. National Stage.
PCT Written Opinion dated May 21, 2008 in the International (PCT) Application PCT/EP2008/051836 of which the present application is the U.S. National Stage.
Weiping Chen et al., "Stereoselective Synthesis of Ferrocene-Based C₂-Symmetric Diphosphine Ligands: Application to the Highly Enantioselective Hydrogenation of α-Substituted Cinnamic Acids", Angewandte Chemie, International Edition, vol. 46, No. 22, pp. 4141-4144, XP009100217, ISSN: 1433-7851, May 25, 2007.
Ulrike Nettekoven et al., "Steric and Electronic Ligand Perturbations in Catalysis: Asymmetric Allylic Substitution Reactions Using C₂-Symmetrical Phosphorus-Chiral (Bi)ferrocenyl Donors", Journal of Organic Chemistry, vol. 66, No. 3, pp. 759-770, XP002325578, ISSN: 0022-3263, Oct. 1, 2001.
Jere D. Fellmann et al., Phosphorus- And Arsenic-Bridged [1]Ferrocenophanes. 3. Hydroformylation Catalyzed by the Products of the Interaction of Co₂(CO)₈, with 1,1'-Ferrocenylenephenylphosphine Oligomers and Polymers, Organometallics, vol. 2, No. 7, pp. 818-825, XP009100216, ISSN: 0276-7333, 1983.
Howard P. Withers et al., "Phosphorus- and Arsenic-Bridged [1]Ferrocenophanes. 2. Synthesis of Poly((1,1'-ferrocenediyl)phenylphosphine) Oligomers and Polymers", Organometallics, vol. 1, No. 10, pp. 1283-1288, XP009100215, ISSN: 0276-7333, 1982.

*Primary Examiner* — Porfirio Nazario Gonzalez
(74) *Attorney, Agent, or Firm* — Wenderoth, Lind & Ponack, L.L.P.

(57) ABSTRACT

Abstract Compounds of the formula (I) in the form of racemates, enantiomerically pure diastereomers or a mixture of diastereomers, where the radicals $R_1$ are identical or different and are each $C_1$-$C_4$-alkyl; m is 0 or an integer from 1 to 4; n is 0 or an integer from 1 to 3; p is 0 or an integer from 1 to 5; $R_2$ is an aromatic hydrocarbon radical or a C-bonded heterohydrocarbon radical and $R_3$ is an aliphatic or C-bonded heteroaliphatic hydrocarbon radical; $R_2$ and $R_3$ are identical or different and are each an aliphatic or C-bonded heteroaliphatic hydrocarbon radical; $R_4$ is an unsubstituted or $C_1$-$C_6$-alkyl-, $C_1$-$C_6$-alkoxy- or halogen-substituted hydrocarbon radical; and A is a secondary amino group, are ligands for metal complexes which are suitable as catalysts for homogeneous enantioselective hydrogenation.

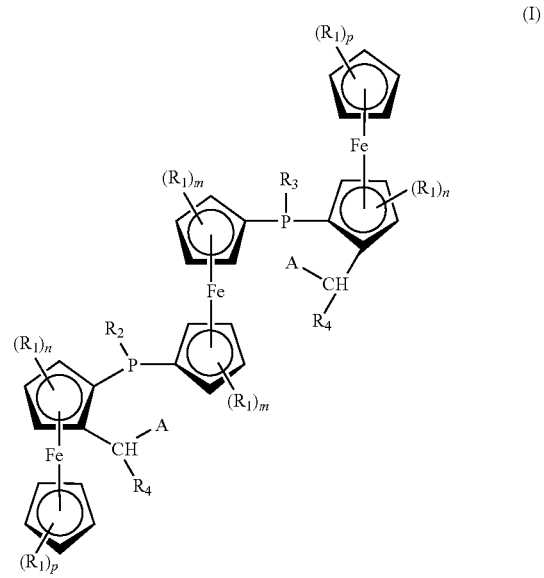

21 Claims, No Drawings

BIS(FERROCENYLPHOSPHINO) FERROCENE LIGANDS USED IN ASYMMETRIC HYDROGENATION REACTIONS

The present invention relates to ferrocene-1,1'-diphosphines in which an α-substituted ferrocenyl radical is bound to each of their two P atoms and the second substituents on the P atoms are either identical or different aliphatic hydrocarbon radicals on the two P atoms or an aromatic, C-bonded radical on the first P atom and an aliphatic hydrocarbon radical on the second P atom. The invention also relates to complexes of transition metals with these ferrocene-1,1'-diphosphines as ligands and to a process for the asymmetric hydrogenation of prochiral organic compounds in the presence of such a metal complex as catalyst.

Chiral ligands such as organic diphosphines have been found to be extraordinarily important auxiliaries for catalysts in homogeneous stereoselective catalysis. Metal complexes by means of which it is possible to achieve not only a satisfactory catalytic activity but also a high stereoselectivity are of practical use. Without these two properties, use in industrial processes is not ensured for economic reasons or uneconomical processes have to be operated because of the lack of alternatives. To avoid such uneconomical processes, many different chiral diphosphines have been made available in recent decades.

Ferrocene is a very useful skeleton for the preparation of ligands and has been used successfully for providing various substitutions with secondary phosphino radicals. Furthermore, diphosphine ligands having a ferrocene skeleton and containing a stereogenic P atom have become known, see, for example, C. Gambs et al., Helvetica Chimica Acta volume 84 (2001), pages 3105-3126, or WO 2005/068477. However, such diphosphines have not achieved any practical importance since the preparation of pure diastereomers is complicated and the diastereomers frequently tend to undergo an undesirable epimerization.

WO 2006/075166 and WO 2006/075177 describe diphosphines and diarsines which are bound via a bridging group and to whose P or As atoms a ferrocenyl radical which is substituted in the α-position relative to the P or As bond by a chiral group is bound. The only specific diphosphine having a 1,1'-ferrocenylene bridge is 1,1'-bis-[($S_p$,$R_c$,$S_{Fe}$)(1-N,N-dimethylamino)ethylferrocenyl)phenylphosphino]ferrocene, which thus contains a phenyl group as further substituent on P. This ligand gives high optical selectivities in the hydrogenation of α,β-unsaturated carboxylic acids. However, the catalyst activity is still unsatisfactory and the hydrogenation is also uneconomical since long reaction times are necessary to achieve high conversions. In addition, the catalyst productivity is also still unsatisfactory since complete conversion can only be achieved at a relatively low ratio of substrate to catalyst. At higher ratios, the conversion decreases sharply.

It has now surprisingly been found that the catalyst activity of metal complexes with this ligand type can be increased quite considerably and symmetric hydrogenations can therefore also be carried out economically at high ratios of substrate to catalyst when one P atom is substituted by a C-bonded aromatic radical and the other P atom is substituted by an aliphatic radical. Furthermore, it has surprisingly been found that a further substantial increase in the catalyst activity can be achieved when the two P atoms are substituted only by aliphatic radicals which can be identical or different. It has also surprisingly been found that despite these increases in activity and productivity, excellent and sometimes improved optical selectivities can still be achieved.

The invention firstly provides compounds of the formula I in the form of racemates, enantiomerically pure diastereomers or a mixture of diastereomers,

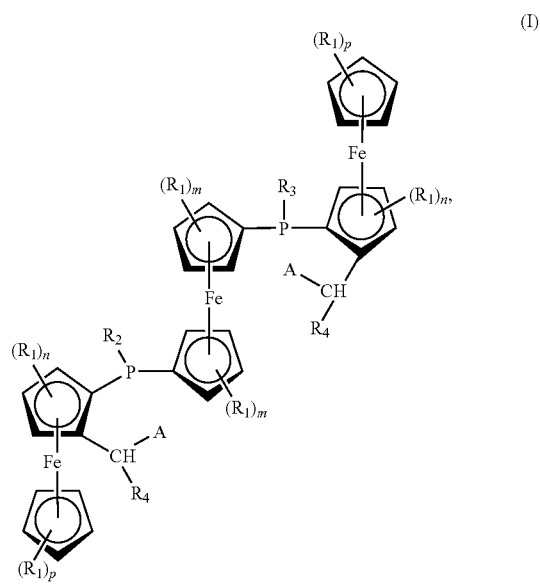

(I)

where
the radicals $R_1$ are identical or different and are each $C_1$-$C_4$-alkyl;
m is 0 or an integer from 1 to 4;
n is 0 or an integer from 1 to 3;
p is 0 or an integer from 1 to 5;
$R_2$ is an aromatic hydrocarbon radical or a C-bonded aromatic heterohydrocarbon radical and $R_3$ is an aliphatic or C-bonded heteroaliphatic hydrocarbon radical;
$R_2$ and $R_3$ are identical or different and are each an aliphatic or C-bonded heteroaliphatic hydrocarbon radical;
$R_4$ is an unsubstituted or $C_1$-$C_6$-alkyl-, $C_1$-$C_6$-alkoxy- or halogen-substituted hydrocarbon radical; and
A is a secondary amino group.

An alkyl group $R_1$ can be, for example, methyl, ethyl, n- or i-propyl, n-, i- or t-butyl, with methyl being preferred. Preference is given to m and/or n being 1 and particularly preferably 0 ($R_1$ is in this case a hydrogen atom) and/or p being 5 and particularly preferably 0.

The hydrocarbon radicals $R_2$ and $R_3$ can be unsubstituted or substituted and/or contain heteroatoms selected from the group consisting of O, S, —N═, —NH— and N($C_1$-$C_4$-alkyl). The aliphatic radicals can contain from 1 to 22, preferably from 1 to 18, particularly preferably from 1 to 12 and very particularly preferably from 1 to 8, carbon atoms and from 0 to 4, preferably 0, 1 or 2, of the heteroatoms mentioned. The aromatic and heteroaromatic radicals can contain from 3 to 22, preferably from 3 to 18, particularly preferably from 4 to 14 and very particularly preferably from 4 to 10, carbon atoms and from 1 to 4, preferably 1 or 2, of the heteroatoms mentioned.

Aromatic radicals $R_2$ can be radicals selected from the group consisting of $C_6$-$C_{14}$-aryl and $C_4$-$C_{12}$-heteroaryl which are unsubstituted or substituted by halogen (fluorine, chlorine or bromine), $C_1$-$C_6$-alkyl, trifluoromethyl, $C_1$-$C_6$-alkoxy, trifluoromethoxy, $(C_6H_5)_3$Si, $(C_1$-$C_{12}$-alkyl)$_3$Si or sec-amino.

Heteroaryls preferably contain heteroatoms selected from the group consisting of O, S, —N($C_1$-$C_4$-alkyl)- and —N=.

Examples of an aryl radical $R_2$ are phenyl, naphthyl, anthracenyl, fluorenyl and benzyl. Examples of a heteroaryl radical $R_2$ are furyl, thiophenyl, N-methylpyrrolidinyl, pyridyl, benzofuranyl, benzothiophenyl and quinolinyl. Examples of substituted aryl, aralkyl, heteroaryl and heteroaralkyl radicals $R_2$ are phenyl, naphthyl, furyl, thio-phenyl, benzofuryl and benzothiophenyl which are substituted by from 1 to 3 radicals selected from the group consisting of methyl, ethyl, n- and i-propyl, n-, i- and t-butyl, ethoxy, methoxy, trifluoromethyl, trifluoromethoxy, fluorine and chlorine. Some preferred examples are 2-, 3- or 4-methylphenyl, 2,4- or 3,5-dimethylphenyl, 3,4,5-trimethylphenyl, 4-ethylphenyl, 2-, 3- or 4-methoxyphenyl, 2,4- or 3,5-dimethoxy-phenyl, 3,4,5-trimethoxyphenyl, 2-, 3- or 4-trifluoromethylphenyl, 2,4- or 3,5-di(tri-fluoromethyl)phenyl, tristrifluoromethylphenyl, 2- or 4-trifluoromethoxyphenyl, 3,5-bis-trifluoromethoxyphenyl, 2- or 4-fluorophenyl, 2- or 4-chlorophenyl and 3,5-dimethyl-4-methoxyphenyl.

In a particularly preferred embodiment, an aryl or heteroaryl radical $R_2$ is o-furyl, phenyl, naphthyl, 2-($C_1$-$C_6$-alkyl)$C_6H_4$, 3-($C_1$-$C_6$-alkyl)$C_6H_4$, 4-($C_1$-$C_6$-alkyl)$C_6H_4$, 2-($C_1$-$C_6$-alkoxy)$C_6H_4$, 3-($C_1$-$C_6$-alkoxy)$C_6H_4$, 4-($C_1$-$C_6$-alkoxy)$C_6H_4$, 2-(trifluoro-methyl)$C_6H_4$, 3-(trifluoromethyl)$C_6H_4$, 4-(trifluoromethyl)$C_6H_4$, 3,5-bis(trifluoro-methyl)$C_6H_3$, 3,5-bis($C_1$-$C_6$-alkyl)$_2C_6H_3$, 3,5-bis($C_1$-$C_6$-alkoxy)$_2$ $C_6H_3$ and 3,5-bis($C_1$-$C_6$-alkyl)$_2$-4-($C_1$-$C_6$-alkoxy)$C_6H_2$.

An aliphatic or C-bonded heteroaliphatic hydrocarbon radical $R_2$ can be a radical selected from the group consisting of linear or branched $C_1$-$C_{12}$-alkyl and preferably α-branched $C_3$-$C_{12}$-alkyl; linear or branched $C_2$-$C_{12}$-heteroalkyl; unsubstituted or $C_1$-$C_6$-alkyl- or $C_1$-$C_6$-alkoxy-substituted $C_4$-$C_{12}$-cycloalkyl or $C_4$-$C_{12}$-cycloalkyl-$CH_2$—; unsubstituted or $C_1$-$C_6$-alkyl- or $C_1$-$C_6$-alkoxy-substituted $C_3$-$C_{12}$-heterocycloalkyl or $C_3$-$C_{12}$-heterocycloalkyl-$CH_2$—; $C_7$-$C_{14}$-aralkyl; and $C_4$-$C_{12}$-heteroaralkyl; with cyclic radicals being able to be substituted by halogen (fluorine, chlorine or bromine), $C_1$-$C_6$-alkyl, trifluoromethyl, $C_1$-$C_6$-alkoxy, trifluoromethoxy, $(C_6H_5)_3Si$, $(C_1$-$C_{12}$-alkyl)$_3Si$, or sec-amino. Preferred heteroatoms are selected from the group consisting of O, S, —NH— and —N($C_1$-$C_4$-alkyl)-.

Examples of alkyl radicals $R_2$ and $R_3$, which preferably contain from 1 to 6 carbon atoms, are methyl, ethyl, n-propyl, i-propyl, n-butyl, i-butyl, t-butyl and the isomers of pentyl and hexyl. Examples of unsubstituted or alkyl- or alkoxy-substituted cycloalkyl groups $R_2$ and $R_3$ are cyclobutyl, cyclopentyl, cyclohexyl, methylcyclohexyl and ethylcyclohexyl, dimethylcyclohexyl, cycloheptyl, cyclooctyl, norbornyl and adamantyl. Examples of unsubstituted or alkyl- or alkoxy-substituted $C_5$-$C_{12}$-cycloalkyl-$CH_2$— groups $R_2$ and $R_3$ are cyclopentylmethyl, cyclohexylmethyl, cyclooctylmethyl, methylcyclohexylmethyl and dimethylcyclohexylmethyl. Examples of substituted or unsubstituted aralkyl or heteroaralkyl groups $R_2$ and $R_3$ are benzyl, methylbenzyl and furylmethyl. Examples of heteroalkyl groups $R_2$ and $R_3$ are methoxymethyl, methoxyethyl, methylthiomethyl and dimethylaminomethyl or dimethylaminoethyl. Examples of unsubstituted or alkyl- or alkoxy-substituted heterocycloalkyl groups $R_2$ and $R_3$ are pyrrolidinyl, piperidinyl and tetrahydrofuranyl. Examples of unsubstituted or alkyl- or alkoxy-substituted heterocycloalkylmethyl groups $R_2$ and $R_3$ are pyrrolidinylmethyl, piperidinylmethyl and tetrahydrofuranyl-methyl. For the purposes of the present invention, the term cycloalkyl also encompasses polycyclic, bridged and optionally fused ring systems such as norbornyl or adamantyl.

In a particularly preferred embodiment, $R_2$ and $R_3$ are each, independently of one another, $C_1$-$C_6$-alkyl, $C_5$-$C_8$-cycloalkyl, $C_5$-$C_8$-cycloalkylmethyl or $C_7$-$C_{10}$-polycycloalkyl.

In a further particularly preferred embodiment, $R_2$ is o-furyl, phenyl, naphthyl, 2-($C_1$-$C_6$-alkyl)$C_6H_4$, 3-($C_1$-$C_6$-alkyl)$C_6H_4$, 4-($C_1$-$C_6$-alkyl)$C_6H_4$, 2-($C_1$-$C_6$-alkoxy)$C_6H_4$, 3-($C_1$-$C_6$-alkoxy)$C_6H_4$, 4-($C_1$-$C_6$-alkoxy)$C_6H_4$, 2-(trifluoromethyl)$C_6H_4$, 3-(trifluoro-methyl)$C_6H_4$, 4-(trifluoromethyl)$C_6H_4$, 3,5-bis(trifluoromethyl)$C_6H_3$, 3,5-bis($C_1$-$C_6$-alkyl)$_2C_6H_3$, 3,5-bis($C_1$-$C_6$-alkoxy)$_2C_6H_3$ and 3,5-bis($C_1$-$C_6$-alkyl)$_2$-4-($C_1$-$C_6$-alkoxy)$C_6H_2$ and $R_3$ is $C_1$-$C_6$-alkyl, $C_5$-$C_8$-cycloalkyl, $C_5$-$C_8$-cycloalkylmethyl or $C_7$-$C_{10}$-polycycloalkyl.

The hydrocarbon radicals $R_4$ can contain from 1 to 18, preferably from 1 to 12, particularly preferably from 1 to 8 and very particularly preferably from 1 to 4, carbon atoms. $R_4$ can be a radical selected from the group consisting of linear or branched $C_1$-$C_8$-alkyl; unsubstituted or halogen (F, Cl or Br)—, $C_1$-$C_6$-alkyl- or $C_1$-$C_6$-alkoxy-substituted $C_4$-$C_8$-cycloalkyl or $C_4$-$C_8$-cycloalkyl-$CH_2$—; unsubstituted or halogen (F, Cl or Br)—, $C_1$-$C_6$-alkyl- or $C_1$-$C_6$-alkoxy-substituted $C_6$-$C_{14}$-aryl or $C_7$-$C_{14}$-aralkyl.

Preferred substituents for $R_4$ are F, Cl, Br, $C_1$-$C_4$-alkyl, in particular methyl or ethyl, and $C_1$-$C_4$-alkoxy, in particular methoxy or ethoxy.

In a preferred embodiment, $R_4$ is $C_1$-$C_4$-alkyl, in particular methyl, $C_5$-$C_6$-cycloalkyl, phenyl, $C_1$-$C_4$-alkylphenyl or $C_1$-$C_4$-alkylbenzyl. $R_4$ is very particularly preferably methyl.

The secondary amino group can correspond to the formula —$NR_5R_6$, where $R_5$ and $R_6$ are identical or different and are each $C_1$-$C_8$-alkyl, $C_5$-$C_8$-cycloalkyl, phenyl or benzyl or $R_5$ and $R_6$ together with the N atom form a five- to eight-membered ring. $R_5$ and $R_6$ are preferably identical radicals and are preferably each $C_1$-$C_4$-alkyl such as methyl, ethyl, n-propyl, i-propyl or n- or i-butyl or together are tetramethylene, pentamethylene or 3-oxa-1,5-pentylene.

$R_5$ and $R_6$ are preferably each methyl or ethyl. Very particularly preferred groups —$CHR_4$-A are 1-dimethylaminoeth-1-yl and 1-(dimethylamino)-1-phenylmethyl.

The compounds of the formula I can be prepared in a simple and modular fashion in high yields even as enantiomerically pure diastereomers. Intermediates can frequently be obtained as enantiomerically pure diastereomers, which makes the preparation of pure diastereomeric end products easier. It is advantageous to start out from 1,1'-dihaloferrocene, which is commercially available, for example 1, 1'-dibromoferrocene, and in which a halogen can be selectively replaced by a metal by means of metallation reagents such as alkyllithium.

In a first variant, the group $R_3$HalP— is introduced by reaction of 1-bromo-1'-lithio-ferrocene with $R_3$—P(Hal)$_2$. Reaction with ortho-metallated ferrocenes substituted by the group —$CHR_4$-A leads to a central intermediate of the formula B which can be obtained as pure diastereomer by heating and subsequent, for example, recrystallization or chromatographic purification:

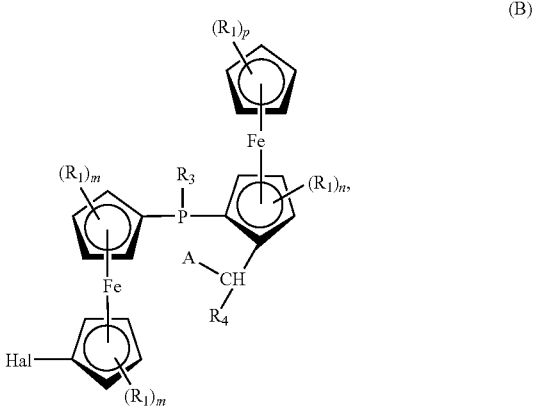

(B)

where Hal is halogen (Cl, Br or I, preferably Br) and m, n, p, A, $R_3$ and $R_4$ are as defined for the compounds of formula I.

In a second variant, the compounds of the formula B can be prepared by reacting an unsubstituted or $R_1$-substituted 1-halo-1'-lithioferrocene with an unsubstituted or $R_1$-substituted 1-(CHR$_4$-A)-2-(R$_3$)PHal-ferrocene, where Hal is halogen (Cl, Br or I, preferably Cl).

The compounds of the formula B can be metallated again (replacement of Hal) and reacted with an unsubstituted or $R_1$-substituted 1-(CHR$_4$-A)-2-(R$_2$)PHal-ferrocene to give compounds of the formula I (Hal is preferably Cl). As an alternative variant, the group R$_2$HalP— (Hal is preferably Cl) can be introduced into a metallated compound of the formula B by reaction with R$_2$—P(Hal)$_2$. The reaction with an unsubstituted or R$_1$— substituted 1-(CHR$_4$-A)-2-Li-ferrocene then leads to a compound of the formula I.

The preparation of the compounds of the formula B usually gives mixtures of diastereomers of the P-chiral compounds. Mixtures of diastereomers of compounds of the formula B can be separated into the various stereoisomers by known methods, for example chromatography.

The compounds of the formula I are generally obtained as mixtures of diastereomers. These mixtures can be at least greatly enriched in the desired diastereomers in a surprisingly simple manner by simple thermal treatment, and pure diastereomers may; if appropriate, be obtained by subsequent recrystallization and/or chromatographic separation. The thermal treatment can be effected, for example, by taking up the reaction product in an inert carrier (solvent) and heating at from 40 to 200° C., preferably from 60 to 160° C., for a period of minutes to hours, for example from 30 minutes to 10 hours. It is more advantageous to treat the solid extracted residue thermally after removal of solvents. The desired diastereomers can in this way be obtained in a high yields and purities.

The dihaloferrocenes and dihalophosphines used are known, some of them are commercially available or they can be prepared by analogous methods. Metallated ferrocenes are known or can be prepared by known or analogous methods. Preference is given to proceeding from known CHR$_4$-A-substituted ferrocenes, metallating these in the ortho position and then reacting them with dihalophosphines. The metallation of ferrocenes by means of alkyllithium or magnesium Grignard compounds involves known reactions which are described, for example, by T. Hayashi et al., Bull. Chem. Soc. Jpn. 53 (1980), pages 1138-1151 or in Jonathan Clayden Organolithiums Selectivity for Synthesis (Tetrahedron Organic Chemistry Series), Pergamon Press (2002). The alkyl in the alkyllithium can contain, for example, from 1 to 6 carbon atoms and preferably from 1 to 4 carbon atoms. Use is frequently made of methyllithium, s-butyllithium, n-butyllithium and t-butyllithium. Magnesium Grignard compounds are preferably those of the formula (C$_1$-C$_4$-alkyl)MgX$_0$, where X$_0$ is Cl, Br or I.

The novel compounds of the formula I are ligands for transition metal complexes which are excellent catalysts or catalyst precursors for asymmetric syntheses, for example the asymmetric hydrogenation of prochiral, unsaturated, organic compounds. If prochiral unsaturated organic compounds are used, a very high excess of optical isomers can be induced in the synthesis of organic compounds and a high chemical conversion can be achieved in short reaction times. The enantioselectivities and catalyst activities which can be achieved are excellent. Furthermore, such ligands can also be used in other asymmetric catalytic reactions, for example addition or cyclization reactions.

The invention further provides complexes of metals selected from the group of transition metals, for example TM8 metals (groups 8, 9 and 10 of the Periodic Table of the Elements), with one of the compounds of the formula I as ligand. For the purposes of the invention, preferred transition metals are metals of groups 7, 8, 9, 10 and 11 of the Periodic Table of the Elements.

Possible metals are, for example, Cu, Ag, Au, Fe, Ni, Co, Rh, Pd, Ir, Ru and Pt. Preferred metals are rhodium and iridium and also ruthenium, platinum and palladium.

Particularly preferred metals are ruthenium, rhodium and iridium.

The metal complexes can, depending on the oxidation number and coordination number of the metal atom; contain further ligands and/or anions. The complexes can also be cationic metal complexes. Such analogous metal complexes and their preparation are widely described in the literature.

The metal complexes can, for example, correspond to the general formulae II and III, $$A_1MeL_r \quad\quad (II),$$

$$(A_1MeL_r)^{(z+)}(E^-)_z \quad\quad (III),$$

where $A_1$ is one of the compounds of the formula I,
L represents identical or different monodentate, anionic or nonionic ligands or L represents identical or different bidentate, anionic or nonionic ligands;
r is 2, 3 or 4 when L is a monodentate ligand or r is 1 or 2 when L is a bidentate ligand;
z is 1, 2 or 3;
Me is a metal selected from the group consisting of Rh, Ir and Ru; with the metal having the oxidation state 0, 1, 2, 3 or 4;
E$^-$ is the anion of an oxo acid or complex acid; and
the anionic ligands balance the charge of the oxidation state 1, 2, 3 or 4 of the metal.

The preferences and embodiments described above apply to the compounds of the formula I.

Monodentate nonionic ligands can, for example, be selected from the group consisting of olefins (for example ethylene, propylene), solvating solvents (nitriles, linear or cyclic ethers, unalkylated or N-alkylated amides and lactams, amines, phosphines, alcohols, carboxylic esters, sulfonic esters), nitrogen monoxide and carbon monoxide.

Suitable polydentate anionic ligands are, for example, allyls (allyl, 2-methallyl) or deprotonated 1,3-diketo compounds such as acetylacetonate.

Monodentate anionic ligands can, for example, be selected from the group consisting of halide (F, Cl, Br, I), pseudohalide (cyanide, cyanate, isocyanate) and anions of carboxylic acids, sulfonic acids and phosphonic acids (carbonate, formate, acetate, propionate, methylsulphonate, trifluoromethylsulphonate, phenylsulphonate, tosylate).

Bidentate nonionic ligands can, for example, be selected from the group consisting of linear or cyclic diolefins (for example hexadiene, cyclooctadiene, norbornadiene), dinitriles (malononitrile), unalkylated or N-alkylated carboxylic diamides, diamines, diphosphines, diols, dicarboxylic diesters and disulphonic diesters.

Bidentate anionic ligands can, for example, be selected from the group consisting of anions of dicarboxylic acids, disulphonic acids and diphosphonic acids (for example oxalic acid, malonic acid, succinic acid, maleic acid, methylenedisulphonic acid and methylenediphosphonic acid).

Preferred metal complexes also include those in which E is $-Cl^-$, $-Br^-$, $-I^-$, $ClO_4^-$, $CF_3SO_3^-$, $CH_3SO_3^-$, $HSO_4^-$, $(CF_3SO_2)_2N^-$, $(CF_3SO_2)_3C^-$, tetraarylborates such as B(phenyl)$_4^-$, B[bis(3,5-trifluoromethyl)phenyl]$_4^-$, B[bis(3,5-dimethyl)phenyl]$_4^-$, B($C_6F_5$)$_4^-$ and B(4-methylphenyl)$_4^-$, $BF_4^-$, $PF_6^-$, $SbCl_6^-$, $AsF_6^-$ or $SbF_6^-$.

Particularly preferred metal complexes which are particularly suitable for hydrogenations correspond to the formulae IV and V, $$[A_1Me_2Y_1Z] \quad (IV),$$

$$[A_1Me_2Y_1]^+E_1^- \quad (V),$$

where
$A_1$ is one of the compounds of the formula I;
$Me_2$ is rhodium or iridium;
$Y_1$ represents two olefins or a diene;
Z is Cl, Br or I; and
$E_1^-$ is the anion of an oxo acid or complex acid.

The embodiments and preferences described above apply to the compounds of the formula I.

An olefin $Y_1$ can be a $C_2$-$C_{12}$—, preferably $C_2$-$C_6$— and particularly preferably $C_2$-$C_4$-olefin. Examples are propene, 1-butene and in particular ethylene. The diene can contain from 5 to 12 and preferably from 5 to 8 carbon atoms and can be an open-chain, cyclic or polycyclic diene. The two olefin groups of the diene are preferably connected by one or two $CH_2$ groups. Examples are 1,4-pentadiene, cyclopentadiene, 1,5-hexadiene, 1,4-cyclohexadiene, 1,4- or 1,5-heptadiene, 1,4- or 1,5-cyclo-heptadiene, 1,4- or 1,5-octadiene, 1,4- or 1,5-cyclooctadiene and norbornadiene. Y preferably represents two ethylenes or is 1,5-hexadiene, 1,5-cyclooctadiene or norbornadiene.

In the formula IV, Z is preferably Cl or Br. Examples of $E_1$ are $BF_4^-$, $ClO_4^-$, $CF_3SO_3^-$, $CH_3SO_3^-$, $HSO_4^-$, B(phenyl)$_4^-$, B[bis(3,5-trifluoromethyl)phenyl]$_4^-$, $PF_6^-$, $AsF_6^-$ or $SbF_6^-$.

The metal complexes of the invention are prepared by methods known from the literature (see also U.S. Pat. Nos. 5,371,256, 5,446,844, 5,583,241 and E. Jacobsen, A. Pfaltz, H. Yamamoto (Eds.), Comprehensive Asymmetric Catalysis I to III, Springer Verlag, Berlin, 1999, and references cited therein).

The metal complexes of the invention are homogeneous catalysts, or catalyst precursors which can be activated under the reaction conditions, which can be used for asymmetric addition reactions onto prochiral, unsaturated, organic compounds.

The metal complexes can be used, for example, for the asymmetric hydrogenation (addition of hydrogen) of prochiral compounds having carbon-carbon or carbon-heteroatom double bonds. Such hydrogenations using soluble metal complexes in homogeneous reaction media are described, for example, in Pure and Appl. Chem., Vol. 68, No. 1, pages 131-138 (1996). Preferred unsaturated compounds to be hydrogenated contain the groups C=C, C=N and/or C=O. According to the invention, metal complexes of ruthenium, rhodium and iridium are preferably used for the hydrogenation.

The invention further provides for the use of the metal complexes of the invention as homogeneous catalysts for the preparation of chiral organic compounds, preferably for the asymmetric addition of hydrogen onto a carbon-carbon or carbon-heteroatom double bond in prochiral organic compounds.

A further aspect of the invention is a process for preparing chiral organic compounds by asymmetric addition of hydrogen onto a carbon-carbon or carbon-heteroatom double bond in prochiral organic compounds in the presence of a catalyst, which is characterized in that the addition reaction is carried out in the presence of catalytic amounts of at least one metal complex according to the invention.

Preferred prochiral, unsaturated compounds to be hydrogenated can contain one or more, identical or different groups C=C, C=N and/or C=O in open-chain or cyclic organic compounds, with the groups C=C, C=N and/or C=O being able to be part of a ring system or exocyclic groups. The prochiral unsaturated compounds can be alkenes, cycloalkenes, heterocycloalkenes and also open-chain or cyclic ketones, α,β-diketones, α- or β-ketocarboxylic acids and their esters and amides, α,β-keto-acetals or -ketals, ketimines and kethydrazones.

Some examples of unsaturated organic compounds are acetophenone, 4-methoxy-acetophenone, 4-trifluoromethylacetophenone, 4-nitroacetophenone, 2-chloroaceto-phenone, corresponding unsubstituted or N-substituted acetophenonebenzylimines, unsubstituted or substituted benzocyclohexanone or benzocyclopentanone and corresponding imines, imines from the group consisting of unsubstituted or substituted tetrahydroquinoline, tetrahyropyridine and dihydropyrrole, and unsaturated carboxylic acids, esters, amides and salts, for example α- and if appropriate β-substituted acrylic acids or crotonic acids. The carboxylic acids can be those of the formula

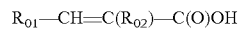

$$R_{01}-CH=C(R_{02})-C(O)OH$$

and also their salts, esters and amides, where $R_{01}$ is a substituted or unsubstituted hydrocarbon radical bound via a carbon atom and $R_{02}$ is linear or branched $C_1$-$C_{18}$-alkyl, unsubstituted or substituted $C_3$-$C_{12}$-cycloalkyl, unsubstituted or substituted $C_6$-$C_{14}$-aryloxy, unsubstituted or substituted $C_1$-$C_{18}$-alkoxy, $C_1$-$C_{18}$-hydroxyalkoxy, $C_1$-$C_{18}$-alkoxy-$C_1$-$C_6$-alkyl or protected amino (for example acetylamino).

The radicals $R_{01}$ and $R_{02}$ can be substituted by one or more, identical or different substituents, for example by protected or unprotected hydroxy, thiol or amino, CN, halogen, $C_1$-$C_6$-alkyl, $C_1$-$C_6$-haloalkyl, $C_1$-$C_6$-alkoxy, $C_1$-$C_6$-alkoxy-$C_1$-$C_4$-alkoxy, $C_6$-$C_{10}$-aryl (preferably phenyl), heteroaryl, ester groups or amide groups.

The hydrocarbon radicals $R_{01}$ can be unsubstituted or substituted and/or contain heteroatoms selected from the group consisting of O, S, —N=, —NH— or N($C_1$-$C_4$-alkyl). Aliphatic hydrocarbon radicals can contain from 1 to 30, preferably from 1 to 22, particularly preferably from 1 to 18 and very particularly preferably from 1 to 12, carbon atoms and from 0 to 4, preferably 0, 1 or 2, of the heteroatoms mentioned. Aromatic and heteroaromatic hydrocarbon radicals can contain from 3 to 22, preferably from 3 to 18, particularly preferably from 4 to 14 and very particularly preferably from 4 to 10, carbon atoms and from 1 to 4, preferably 1 or 2, of the heteroatoms mentioned.

Examples and preferred embodiments of hydrocarbon radicals have been given above for the radicals $R_2$ and $R_3$ and also apply to $R_{O1}$ and $R_{O2}$.

$R_{O1}$ is preferably monocyclic or polycyclic (for example from 2 to 4 rings) $C_6$-$C_{14}$-aryl or $C_3$-$C_{14}$-heteroaryl containing heteroatoms selected from the group consisting of O, S, —N═, —NH— or N($C_1$-$C_4$-alkyl), which may be substituted, for example by protected or unprotected hydroxy, thiol or amino, $C_1$-$C_6$-alkyl, $C_1$-$C_6$-alkoxy, $C_1$-$C_6$-alkoxy-$C_1$-$C_4$-alkoxy, ester groups or amide groups. Aryl and heteroaryl can, for example, be derived from benzene, naphthalene, indane, anthracene, phenanthrene, fluorene, thiophene, furan, pyrrole, pyridine, pyrimidine, pyrazine, benzothiophene, benzo-furan, indole, isoindole and quinoline.

It has surprisingly been found that in the hydrogenation of α-alkyl-β-arylacrylic or β-heteroarylacrylic acids, in particular carboxylic acids of the formula VI, using rhodium complexes and ligands of the formula I as catalysts, it is possible to achieve quite outstanding optical yields of over 97% ee (ee=enantiomeric excess) and a high chemical conversion within short reaction times even at a high ratio of substrate to catalyst of 2000 or above, i.e. a high catalyst activity is observed. The hydro-genation of carboxylic acids of the formula VI using metal complexes of chiral bidentate ligands is described in WO2002/02500 A1.

A particularly preferred embodiment of the process of the invention is characterized in that compounds of the formula VI,

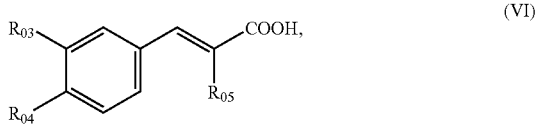

(VI)

where
$R_{O3}$ and $R_{O4}$ are each, independently of one another, H, $C_1$-$C_6$-alkyl, $C_1$-$C_6$-haloalkyl, $C_1$-$C_6$-alkoxy, $C_1$-$C_6$-alkoxy-$C_1$-$C_6$-alkyl or $C_1$-$C_6$-alkoxy-$C_1$-$C_6$-alkyloxy and $R_{O5}$ is $C_1$-$C_6$-alkyl, are hydrogenated by means of hydrogen in the presence of rhodium complexes with ligands of the formula I as catalysts to give compounds of the formula VII

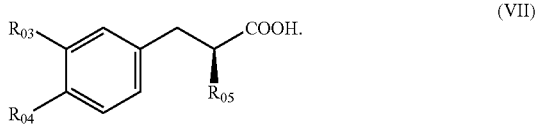

(VII)

$R_{O3}$ is preferably methoxypropyloxy, $R_{O4}$ is preferably methoxy and $R_{O5}$ is preferably isopropyl.

Furthermore, it has surprisingly been found that in the hydrogenation of α-alkoxy-β-arylacrylic or -β-heteroarylacrylic acids, in particular carboxylic acids of the formula VIII, using rhodium complexes and ligands of the formula I as catalysts, it is possible to achieve quite outstanding optical yields of over 97% ee (ee=enantiomeric excess) and a high chemical conversion within short reaction times even at a high ratio of substrate to catalyst of 200 or above, i.e. a high catalyst activity is observed.

A further particularly preferred embodiment of the process of the invention is characterized in that compounds of the formula VIII,

(VIII)

where
$R_{O6}$ is $C_1$-$C_8$-alkyl, protected or unprotected $C_1$-$C_8$-hydroxyalkyl or $C_1$-$C_8$-alkoxy-$C_1$-$C_6$-alkyl and $R_{O7}$ is $C_6$-$C_{14}$-aryl or $C_3$-$C_{14}$-heteroaryl containing heteroatoms selected from the group consisting of O, S, —N═, —NH— or N($C_1$-$C_4$-alkyl), which may be unsubstituted or substituted by protected or unprotected hydroxy, thiol or amino, $C_1$-$C_6$-alkyl, $C_1$-$C_6$-alkoxy, $C_1$-$C_6$-alkoxy-$C_1$-$C_4$-alkoxy, ester groups or amide groups, are hydrogenated to give compounds of the formula IX

(VIII)

$R_{O6}$ is preferably $C_1$-$C_4$-alkyl and $R_{O7}$ is preferably phenyl, naphthyl, thiophenyl, furyl, benzothiophenyl or benzofuryl which may be unsubstituted or substituted by protected or unprotected hydroxy or thiol, $C_1$-$C_6$-alkyl, $C_1$-$C_6$-alkoxy, $C_1$-$C_6$-alkoxy-$C_1$-$C_4$-alkoxy, ester groups or amide groups. Examples of protective groups are benzyl, trityl, trialkylsilyl and aminocarbonyl.

The process of the invention can be carried out at low or elevated temperatures, for example temperatures of from −20 to 150° C., preferably from −10 to 100° C. and particularly preferably from 10 to 80° C. The optical yields are generally better at a, relatively low temperature than at higher temperatures.

The process of the invention can be carried out at atmospheric pressure or super-atmospheric pressure. The pressure can be, for example, from $10^5$ to $2×10^7$ Pa (pascal). Hydrogenations can be carried out at atmospheric pressure or at superatmospheric pressure.

Catalysts are preferably used in amounts of from 0.0001 to 10 mol %, particularly preferably from 0.001 to 10 mol % and very particularly preferably from 0.01 to 5 mol %, based on the compound to be hydrogenated.

The preparation of the ligands and catalysts and also the hydrogenation can be carried out without a solvent or in the presence of an inert solvent, with one solvent or mixtures of solvents being able to be used. Suitable solvents are, for example, aliphatic, cycloaliphatic and aromatic hydrocarbons (pentane, hexane, petroleum ether, cyclohexane, methylcyclohexane, benzene, toluene, xylene), aliphatic halogenated hydrocarbons (methylene chloride, chloroform, dichloroethane and tetrachloroethane), nitriles (acetonitrile, propionitrile, benzonitrile), ethers (diethyl ether, dibutyl ether, t-butyl methyl ether, ethylene glycol dimethyl ether, ethylene glycol diethyl ether, diethylene glycol dimethyl ether, tetrahydrofuran, dioxane, diethylene glycol monomethyl or monoethyl ether), ketones (acetone, methyl isobutyl ketone), carboxylic esters and lactones (ether or methyl acetate, valerolactone), N-substituted lactams (N-methylpyrrolidone), carboxamides (dimethylamide, dimethylformamide), acyclic ureas (dimethylimidazoline) and sulphoxides and sulphones (dimethyl sulphoxide, dimethyl sulphone, tetramethylene sulphoxide, tetramethylene sulphone) and alcohols (methanol, ethanol, propanol, butanol, ethylene glycol monomethyl ether, ethylene glycol monoethyl ether, diethylene glycol monomethyl ether) and water. The solvents can be used either alone or as a mixture of at least two solvents.

The reaction can be carried out in the presence of cocatalysts, for example quaternary ammonium halides (tetrabutylammonium iodide) and/or in the presence of protic acids, for example mineral acids (see, for example, U.S. Pat. Nos. 5,371,256, 5,446,844 and 5,583,241 and EP-A-0 691 949). The presence of fluorinated alcohols such as 1,1,1-trifluoroethanol or of bases (amines, alkali metal hydroxides, carbonates and hydrogencarbonates) can likewise promote the catalytic reaction.

The metal complexes used as catalysts can be added as separately prepared isolated compounds or else can be formed in situ prior to the reaction and then mixed with the substrate to be hydrogenated. It can be advantageous to add additional ligands in the reaction using isolated metal complexes or use an excess of the ligand in the in situ preparation. The excess can be, for example, up to 6 mol and preferably up to 2 mol, based on the metal compound used for the preparation.

The process of the invention is generally carried out by placing the catalyst in a reaction vessel and then adding the substrate, if appropriate reaction auxiliaries and the compound to be added on and subsequently starting the reaction. Gaseous compounds to be added on, for example hydrogen or ammonia, are preferably introduced under pressure. The process can be carried out continuously or batchwise in various types of reactor.

The chiral, organic compounds prepared according to the invention are active sub-stances or intermediates for the preparation of such substances, in particular in the preparation of flavours and fragrances, pharmaceuticals and agrochemicals.

The following examples illustrate the invention. The abbreviations have the following meanings:

TBME=tert-butyl methyl ether, s-BuLi=sec-butyllithium, n-BuLi=n-butyllithium, EtOAc=ethyl acetate, Et₃N=triethylamine, THF=tetrahydrofuran, DE=diethyl ether, TMEDA=tetramethylethylenediamine, nbd=norbornadiene, cod=cycloocta-1,5-diene.

A) Preparation of Intermediates

EXAMPLE A1

Preparation of (R$_c$,S$_{Fc}$,S$_P$)-1-[2-(1-dimethylaminoethyl)ferrocen-1-yl]phenylphosphino-1'-bromoferrocene of the formula (A1) [Ph=phenyl; Me=methyl]

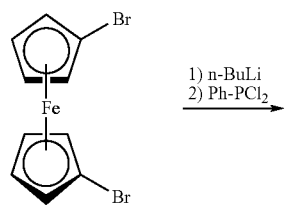

a) Preparation of 1-phenylchlorophosphino-1'-bromoferrocene (X1)

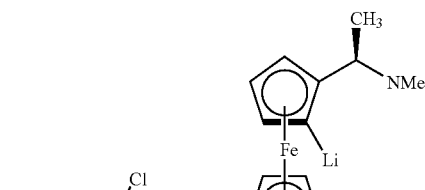
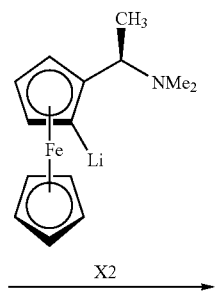

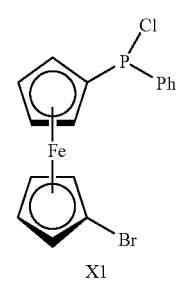

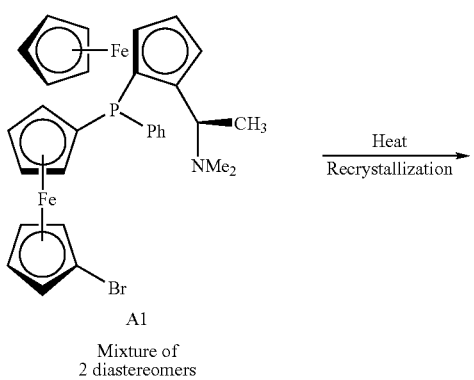

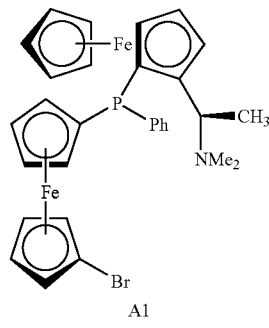

14.5 ml (23.2 mmol) of n-BuLi (1.6 M in hexane) are added dropwise to a solution of 8 g (23.2 mmol) of 1,1'-dibromoferrocene in 30 ml of THF at a temperature of <−30° C. The mixture is stirred for another 30 minutes at this temperature. It is then cooled to −78° C. and 3.15 ml (23.2 mmol) of phenyldichlorophosphine are added dropwise at such a rate that the temperature does not exceed −60° C. After stirring at −78° C. for a further 10 minutes, the temperature is allowed to rise to room temperature and the mixture is stirred for another one hour. This gives a suspension of the monochlorophosphine X1.

b) Preparation of A1 (Mixture of Diastereomers)

15.5 ml (23.2 mmol) of t-butyllithium (t-BuLi) (1.5 M in pentane) are added dropwise to a solution of 5.98 g (23.2 mmol) of (R)-1-dimethylamino-1-ferrocenylethane in 40 ml of DE at <−10° C. After stirring for 10 minutes at the same temperature, the temperature is allowed to rise to room temperature and the mixture is stirred for another 1.5 hours. This gives a solution of the compound X2 which is added via a cannula to the cooled suspension of the monochlorophosphine X1 at such a rate that the temperature does not exceed −30° C. After stirring at −30° C. for a further 10 minutes, the temperature is allowed to rise to 0° C. and the mixture is stirred at this temperature for another 2 hours. The reaction mixture is admixed with 20 ml of water. The organic phase is separated off, dried over sodium sulphate and the solvent is distilled off under reduced pressure on a rotary evaporator. Purification by chromatography (silica gel 60; eluent=heptane/EtOAc/Et$_3$N 85:10:5) gives 11.39 g of the desired product as a mixture of 2 diastereomers.

c) Preparation of A1 (One Diastereomer)

If desired, the mixture of diastereomers can be converted into a single diastereomer by thermal treatment, as follows. The product obtained in process step b) is dissolved in 50 ml of toluene and refluxed for 4 hours. After distilling off the toluene, the residue is recrystallized from ethanol. This gives the compound X3 as yellow crystals and as a pure diastereomer in a yield of 59% of theory. $^{31}$P-NMR (121.5 MHz), CDCl$_3$): δ−35.3 (s).

EXAMPLE A2

Preparation of (R$_C$,S$_{Fc}$,S$_P$)-1-[2-(1-dimethylaminoethyl)ferrocen-1-yl]cyclo-hexylphosphino-1′-bromoferrocene of the formula (A2) [Cy=cyclohexyl; Me=methyl]

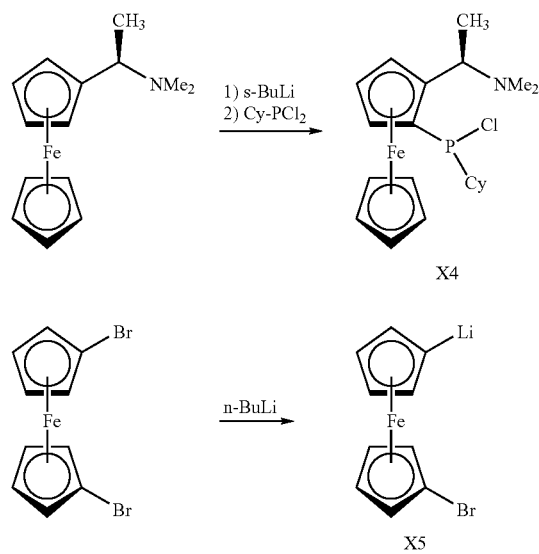

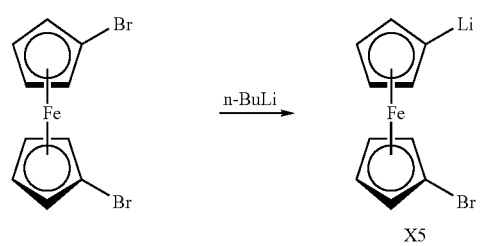

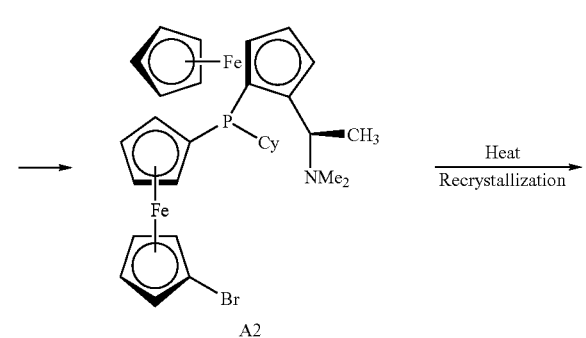

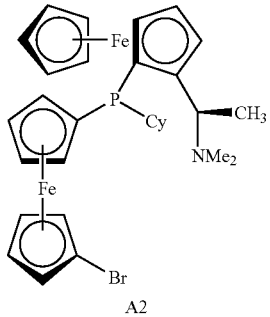

a) Preparation of the Monochlorophosphine X4

1.3 M s-BuLi solution in cyclohexane (7.7 ml, 10 mmol) is added to a solution of (R)-N,N-dimethyl-1-ferrocenylethylamine[(R)-Ugi amine] (2.57 g, 10 mmol) in TBME (15 ml) over a period of 10 minutes and at a temperature below −20° C. After the addition is complete, the reaction mixture is warmed to 0° C. and stirred at this temperature for 1.5 hours. Dichlorocyclohexylphosphine (1.51 ml, 10 mmol) is then added at a temperature below −60° C. over a period of 10 minutes. The mixture is then stirred at −78° C. for another 30 minutes, the cooling bath is removed, the reaction mixture is stirred for a further one hour. This gives the monochlorophosphine X4.

b) Preparation of 1-bromo-1'-lithioferrocene X5

4 ml (10 mmol) of n-BuLi (2.5 M in hexane) are added dropwise to a solution of 3.43 g (10 mmol) of 1,1'-dibromoferrocene in 10 ml of tetrahydrofuran (THF) at a temperature of <−30° C. The mixture is stirred at this temperature for another 1.5 hours and subsequently cooled to −78° C. This gives a suspension of 1-bromo-1'-lithioferrocene X5.

c) Preparation of the Compound A2

The reaction mixture a) containing the monochlorophosphine X4 is added dropwise to the suspension b) of 1-bromo-1'-lithioferrocene X5 at a temperature below −20° C. while stirring. The cooling is then removed and the reaction mixture is stirred at room temperature for one hour. This gives compound X6 as a mixture of 2 diastereomers. The reaction mixture can be directly used further for the next reaction step. If required, the intermediate X6 can be worked up, thermally isomerized and isolated as a pure diastereomer in a manner analogous to Example A1c).

As an alternative, the compound A1 can be prepared in a manner analogous to Example A2 or the compound A2 can be prepared in a manner analogous to Example A1.

B) Preparation of Ligands

EXAMPLE 1

Preparation of [($R_C$,$R_C$)($S_{Fc}$,$S_{Fc}$)($S_P$,$S_P$)-1-[2-(1-dimethylaminoethyl)ferrocenyl]phenylphosphino-1'-[2-(1-dimethylaminoethyl)ferrocenyl]cyclohexylphosphinoferrocene of the formula (B1) [R=phenyl; Me=methyl, R'=cyclohexyl]

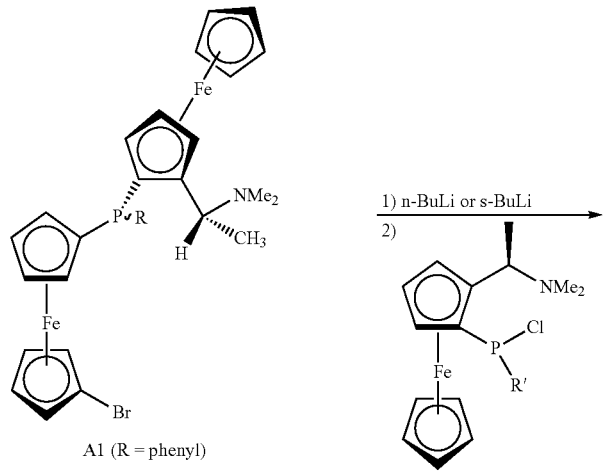

A1 (R = phenyl)

1) n-BuLi or s-BuLi
2)

X7 (R' = cyclohexyl)
X8 (R' = isopropyl)

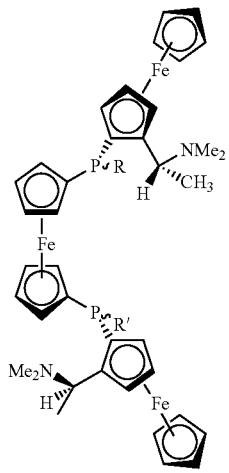

Mixture of diastereomers

B1 (R = phenyl; R' = cyclohexyl)
B2 (R = phenyl; R' = isopropyl)

150° C., 2 h

-continued

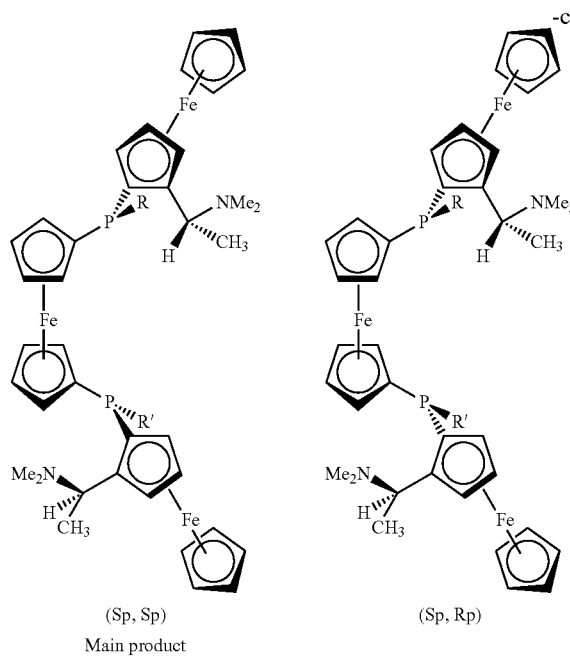
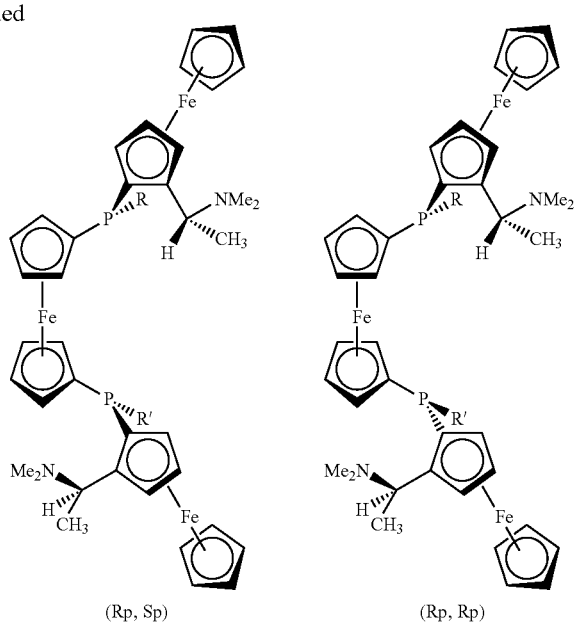

(Sp, Sp)  (Sp, Rp)  (Rp, Sp)  (Rp, Rp)
Main product

Reaction mixture a) 1.3 M s-BuLi solution in cyclohexane (3.85 ml, 5 mmol) is added to a solution of (R)-N,N-dimethyl-1-ferrocenylethylamine[(R)-Ugi amine] (1.28 g, 5 mmol) in TBME (10 ml) over a period of 10 minutes and at a temperature below −20° C. After the addition is complete, the reaction mixture is warmed to 0° C. and stirred at this temperature for another 1.5 hours. Dichlorocyclohexylphosphine (0.76 ml, 5 mmol) is then added at a temperature below −60° C. over a period of 10 minutes. The reaction mixture is then stirred at −78° C. for another 30 minutes, the cooling bath is removed and the reaction mixture is stirred for a further one hour to give the monochlorophosphine X7.

Reaction mixture b) In another reaction vessel, s-BuLi (1.3 M in cyclohexane, 3.85 ml, 5 mmol) is added to a solution of compound A1 (3.15 g, 5 mmol) in TMBE (10 ml) at a temperature below −60° C. and the mixture is then stirred at −78° C. for one hour. This gives a solution of the lithiated compound X3.

c) The reaction mixture b) is added to the reaction mixture a) which has been cooled to −78° C. at such a rate that the temperature does not exceed −60° C. After the addition is complete, the cooling bath is removed and the reaction mixture is stirred for another 1.5 hours. 5 ml of saturated, aqueous $NaHCO_3$ solution are then added while stirring. The organic phase is then separated off, dried over $Na_2SO_4$ and then evaporated to dryness under reduced pressure. The residue is then heated at 150° C. for 2 hours and subsequently purified by chromatography ($SiO_2$: 120 g, firstly hexane:EtOAc=3:1, then hexane:EtOAc=3:1 containing 1% of $Et_3N$). The first fraction gives the pure title compound B1 (2.10 g, 45.7%). The second fraction is a mixture of various diastereomers (1.20 g, 26.1%). The second fraction is again heated at 150° C. for 1.5 hours and purified by chromatography as before. The isolated first fraction gives a further 0.57 g (12.4%) of the pure title compound B1. $^1$H NMR($C_6D_6$, 300 MHz): δ 1.16 (d, J=6.7 Hz, 3H), 1.29 (d, J=.6.7 Hz, 3H), 1.09~2.45 (m, 11H), 1.78 (s, 6H), 2.26 (s, 6H), 3.90 (s, 1H), 4.04 (s, 1H), 4.05 (s, 1H), 4.09 (s, 5H), 4.13 (s, 2H), 4.16 (s, 1H), 4.17 (s, 5H), 4.19 (s, 1H), 4.21 (s, 1H), 4.30 (m, 1H), 4.39~4.44 (m, 3H), 4.53 (s, 1H), 4.59 (s, 1H), 4.85 (m, 2H), 7.24 (m, 3H), 7.85 (m, 2H). $^{31}$P NMR($C_6D_6$, 101 MHz): δ −26.5 and −35.3.

EXAMPLE 2

Preparation of [($R_C,R_C$)($S_{Fc},S_{Fc}$)($S_P,S_P$)-1-[2-(1-dimethylaminoethyl)-ferrocenyl]phenylphosphino-1'-[2-(1-dimethylaminoethyl)ferrocenyl]isopropyl-phosphinoferrocene of the formula (B2) [R=phenyl; Me=methyl, R'=isopropyl]

The compound B2 is prepared in a manner analogous to compound B1 in Example 1, except that isopropyldichlorophosphine is used in place of cyclohexyldichlorophosphine in the reaction mixture a). The crude product is purified by chromatography (silica gel; eluent=firstly ethyl acetate/hexane 1:5, subsequently with an additional 1% of triethylamine). A mixture of two diastereomers (ratio=5:4) is obtained. This is heated at 150° C. without solvent for 2 hours and subsequently purified by chromatography (silica gel; eluent=firstly ethyl acetate/hexane 1:3, subsequently with an additional 1% of triethylamine). The first fraction gives the clean product B2 as an orange solid in a yield of 47.5%. The second fraction (30%) gives a mixture of various diastereomers.

1H NMR($C_6D_6$, 300 MHz): δ1.10~1.17 (m, 6H), 1.28 (d, J=6.7 Hz, 3H), 1.59 (dd, J=18.8 and 6.6 Hz, 3H), 1.77 (s, 6H), 2.24 (s, 6H), 2.59 (m, 1H), 3.90 (br. s, 1H), 4.04 (m, 1H), 4.07 (m, 2H), 4.09 (s, 5H), 4.13 (s, 2H), 4.16 (s, 5H), 4.20 (s, 2H), 4.29 (m, 1H), 4.35 (s, 1H), 4.39 (m, 1H), 4.40 (m, 1H), 4.50 (s, 1H), 4.56 (m, 1H), 4.87 (s, 2H), 7.24 (m, 3H), 7.85 (m, 2H). $^{31}$P NMR($C_6D_6$, 101 MHz): δ−24.1 and −35.3.

The compounds of the formulae B1 and B2 can also be obtained via the following alternative route:

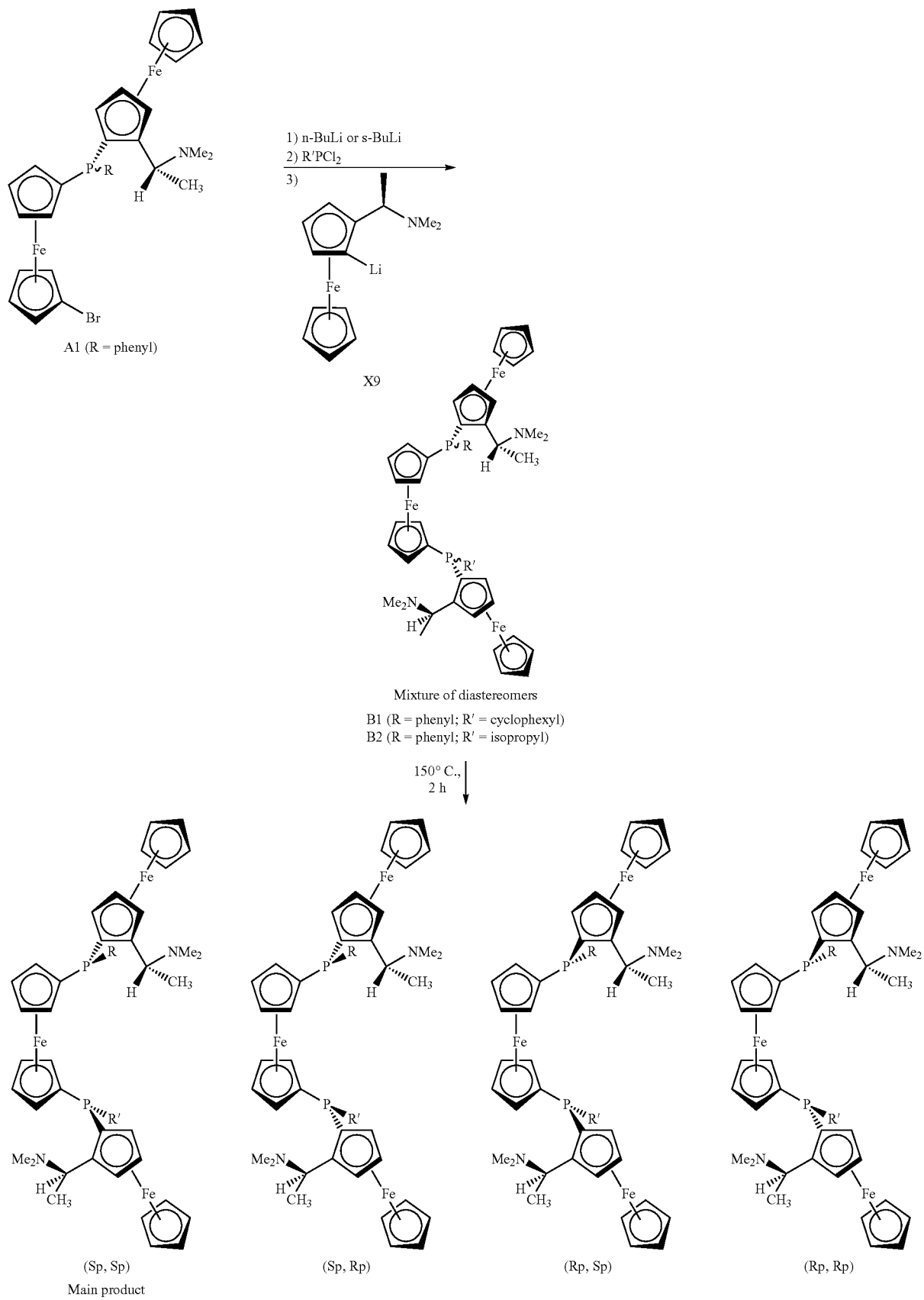

EXAMPLE 3

Preparation of [($R_C,R_C,$)($S_{Fc},S_{Fc},$)($S_P,S_P$)-1-[2-(1-dimethylaminoethyl)-ferrocenyl]phenylphosphino-1'-[2-(1-dimethylaminoethyl)ferrocenyl]cyclohexyl-phosphinoferrocene of the formula (B1) [R=phenyl; Me=methyl, R'=cyclohexyl]

a) 1.3 M s-BuLi solution in cyclohexane (3.85 ml, 5 mmol) is added to a solution of (R)-N,N-dimethyl-1-ferrocenylethylamine[(R)-Ugi amine] (1.28 g, 5 mmol) in TBME (10 ml) over a period of 10 minutes and at a temperature below −20° C. After the addition is complete, the reaction mixture is warmed to 0° C. and stirred at this temperature for another 1.5 hours. This gives the lithiated Ugi amine X9.

b) In another reaction vessel, s-BuLi (1.3 M in cyclohexane, 3.85 ml, 5 mmol) is added to a solution of compound A1 (3.15 g, 5 mmol) in TMBE (10 ml) at a temperature below −60° C. and the mixture is then stirred at −78° C. for one hour. This gives a solution of the lithiated compound X3. Dichlorocyclohexylphosphine (0.76 ml, 5 mmol) is then added at a temperature below −60° C. over a period of 10 minutes. The mixture is then stirred at −78° C. for 30 minutes, the cooling bath is removed and the reaction mixture is stirred for a further one hour.

c) The suspension containing the compound X9 prepared as described in a) is added to the reaction mixture prepared as described in b) at a temperature below −60° C. while stirring. The cooling bath is then removed and the mixture is stirred for a further 1.5 hours. 5 ml of saturated, aqueous $NaHCO_3$ solution are then added while stirring. The organic phase is then separated off, dried over $Na_2SO_4$ and then evaporated to dryness under reduced pressure. The residue is then heated at 150° C. for 2 hours and subsequently purified by chromatography ($SiO_2$: 120 g, first hexane:EtOAc=3:1, then hexane:EtOAc=3:1 containing 1% of $Et_3N$). The first fraction gives the pure title compound B1. The second fraction is a mixture of various diastereomers. The $^1H$ NMR and $^{31}P$ NMR spectra are identical to those of the compound B1 prepared as described in Example B1.

EXAMPLE 4

Preparation of [($R_C,R_C,$)($S_{Fc},S_{Fc},$)($S_P,S_P$)-1-[2-[(1-dimethylaminoethyl)-ferrocenyl]phenylphosphino-1'-[2-(1-dimethylaminoethyl)ferrocenyl]isopropyl-phosphinoferrocene of the formula (B2) [R=phenyl; Me=methyl, R'=isopropyl]

a) 1.3 M s-BuLi solution in cyclohexane (3.08 ml, 4 mmol) is added to a solution of (R)-N,N-dimethyl-1-ferrocenylethylamine[(R)-Ugi amine] (1.03 g, 4 mmol) in TBME (10 ml) over a period of 10 minutes and at a temperature below −20° C. After the addition is complete, the reaction mixture is warmed to 0° C. and stirred at this temperature for another 1.5 hours. This gives the lithiated Ugi amine X9.

b) In another reaction vessel, s-BuLi (1.3 M in cyclohexane, 3.08 ml, 4 mmol) is added to a solution of compound A1 (2.52 g, 4 mmol) in TMBE (5 ml) at a temperature below −60° C. and the mixture is then stirred at −78° C. for one hour. This gives a solution of the lithiated compound X3. Dichloroisopropylphosphine (0.49 ml, 4 mmol) is then added at a temperature below −60° C. over a period of 10 minutes. The mixture is then stirred at −78° C. for 30 minutes, the cooling bath is removed and the reaction mixture is stirred for a further one hour.

c) The suspension prepared as described in a) is added to the reaction mixture pre-pared as described in b) at a temperature below −60° C. while stirring. The cooling bath is then removed and the mixture is stirred for a further 1.5 hours. 5 ml of saturated, aqueous $NaHCO_3$ solution are then added while stirring. The organic phase is then separated off, dried over $Na_2SO_4$ and then evaporated to dryness under reduced pressure. The residue is then heated at 150° C. for 2 hours and subsequently purified by chromatography ($SiO_2$: 120 g, first hexane:EtOAc=3:1, then hexane:EtOAc=3:1 containing 1% of $Et_3N$). The first fraction gives the pure title compound B2. The second fraction is a mixture of various diastereomers. The $^1H$ NMR and $^{31}P$ NMR spectra are identical to those of the compound B2 prepared as described in Example B2.

EXAMPLE 5

Preparation of [($R_C,R_C$),($S_{Fc},S_{Fc}$),($S_P,S_P$)]-1-[2-(1-N,N-dimethylamino-ethyl)-1-ferrocenyl]phenylphosphino-1'-[2-(1-N,N-dimethylaminoethyl)-1-ferrocenyl](4-methoxyphenyl)phosphinoferrocene[($S_P,S_P$)-3c] of the formula (B3)

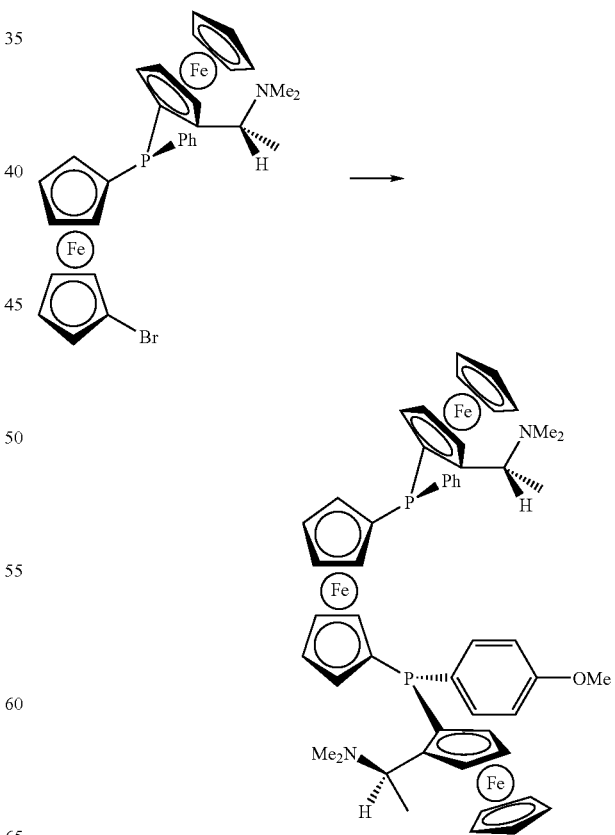

The compound B3 is prepared in a manner analogous to the compound B1 in Example 1, except that 4-methoxyphenyl-dichlorophosphine is used in place of cyclohexyldichlorophosphine in the reaction mixture a). The reaction mixture is quenched with water, resulting in the product precipitating as a yellow solid. Filtration and washing with ethyl acetate gives the pure product B3 in a yield of 64%.

1H NMR (CDCl$_3$, 300 MHz): δ 1.18 (d, J=6.7 Hz, 3H), 1.20 (d, J=6.7 Hz, 3H), 1.52 (s, 6H), 1.57 (s, 6H), 3.44 (br.s, 1H), 3.48 (br. s, 1H), 3.82 (s, 3H), 3.84 (m, 1H), 3.86 (m, 1H), 3.91 (m, 1H), 3.94 (m, 1H), 4.02 (s, 5H), 4.03 (s, 5H), 4.12 (m, 4H), 4.23 (m, 2H), 4.32 (m, 2H), 4.63 (m, 2H), 6.76 (d, J=8.3 Hz, 2H), 7.21 (m, 3H), 7.36 (dd, J=8.3 and 8.1 Hz, 2H), 7.44 (m, 2H); $^{31}$P NMR (CDCl$_3$, 101 MHz): δ −35.3 and −37.5.

EXAMPLE 6

Preparation of [(R$_C$,R$_C$),(S$_{Fc}$,S$_{Fc}$),(S$_P$,S$_P$)]-1-[2-(1-N,N-dimethylamino-ethyl)-1-ferrocenyl]phenylphosphino-1'-[2-(1-N,N-dimethylaminoethyl)-1-ferrocenyl][4-(trifluoromethyl)phenyl]phosphinoferrocene [(S$_P$,S$_P$)-3d] of the formula (B4)

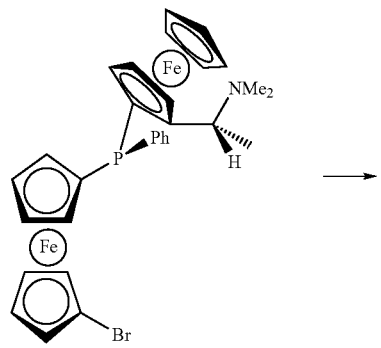

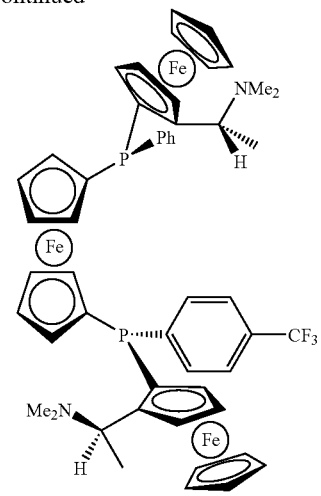

The compound B4 is prepared in a manner analogous to the compound B1 in Example 1; except that 4-trifluoromethylphenyldichlorophosphine is used in place of cyclohexyldichlorophosphine in the reaction mixture a). After the reaction, the reaction mixture is quenched with water and extracted with ethyl acetate. The organic phases are collected, dried over sodium sulphate and the solvent is distilled off on a rotary evaporator. The crude product is heated at 150° C. without solvent for 1 hour and subsequently purified by chromatography (silica gel; eluent=ethyl acetate/hexane 1:5 containing 1% of triethylamine). The product B4 is obtained as an orange solid in a yield of 56%.

1H NMR (CDCl$_3$, 300 MHz): δ 1.11 (d, J=6.7 Hz, 3H), 1.15 (d, J=6.7 Hz, 3H), 1.46 (s, 6H), 1.50 (s, 6H), 3.26 (m, 1H), 3.37 (m, 1H), 3.80 (m, 1H), 3.83 (m, 1H), 4.01 (m, 1H), 4.03 (s, 5H), 4.04 (s, 5H), 4.12 (m, 4H), 4.23 (m, 2H), 4.36 (m, 2H), 4.62 (m, 2H), 7.18 (m, 3H), 7.37~7.52 (m, 6H); $^{31}$P NMR (CDCl$_3$, 101 MHz): δ −34.6 and −35.3.

EXAMPLE 7

Preparation of [(R$_C$,R$_C$),(S$_{Fc}$,S$_{Fc}$),(S$_P$,S$_P$)]-1-[2-(1-N,N-dimethylamino-ethyl)-1-ferrocenyl]isopropylphosphino-1'-[2-(1-N,N-dimethylaminoethyl)-1-ferro-cenyl]cyclohexylphosphinoferrocene of the formula (B5) [R=cyclohexyl; Me=methyl; R'=isopropyl]

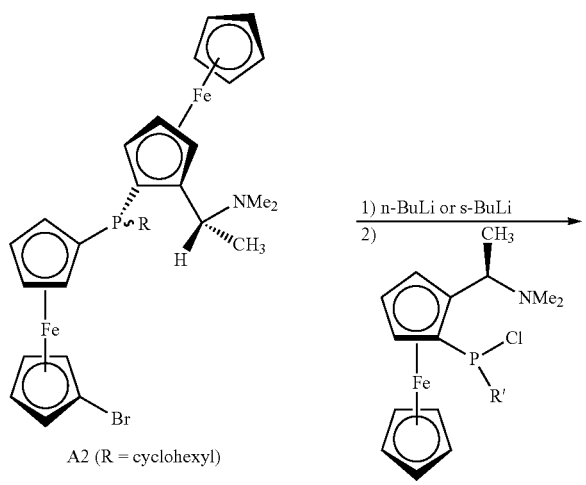

-continued

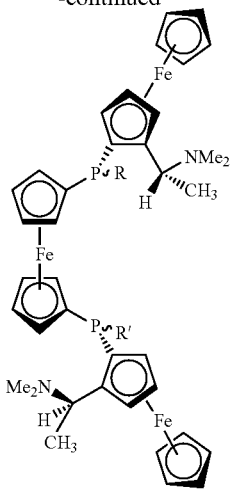

Mixture of diastereomers
B5 (R = cyclohexyl; R' = isopropyl)

150° C.,
2 h

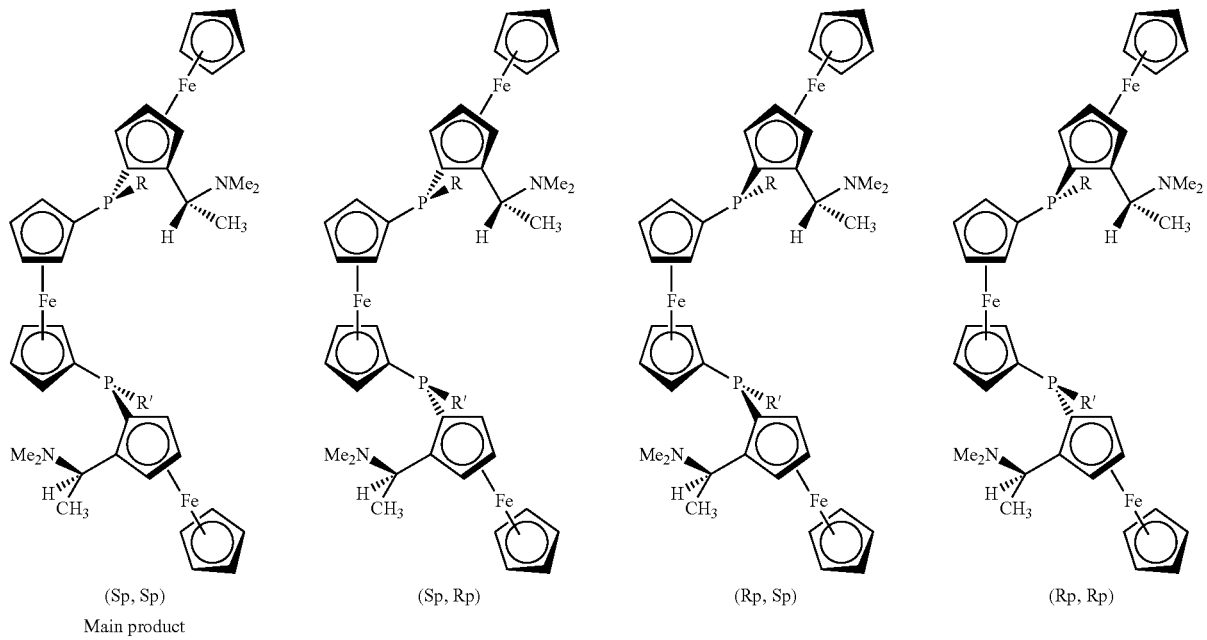

(Sp, Sp)
Main product (Sp, Rp)

(Rp, Sp)

(Rp, Rp)

a) The reaction mixture c) prepared as described in Example A2 (10 mmol batch) is cooled to −50° C. 4 ml (10 mmol) of n-BuLi (2.5 M in hexane) are then added dropwise with the temperature being kept below −30° C. The temperature is then allowed to rise to 0° C., the mixture is stirred at this temperature for 30 minutes and is cooled back down to −50° C. This gives a suspension of $(R_C, S_{Fc})$-1-[2-[1-N,N-dimethylaminoethyl)-1-ferrocenyl]cyclohexylphosphino-1'-lithioferrocene.

b) In a vessel, 7.7 ml (10 mmol) of s-BuLi (1.3 M in cyclohexane) are added to a solution of (R)-N,N-dimethyl-1-ferrocenylethylamine[(R)-Ugi amine] (2.57 g, 10 mmol) in TBME (15 ml) at a temperature below −20° C. over a period of 10 minutes. After the addition is complete, the reaction mixture is warmed to 0° C. and stirred at this temperature for another 1.5 hours. Dichloroisopropylphosphine (1.23 ml, 10 mmol) is then added at a temperature below −60° C. over a period of 10 minutes. The mixture is then stirred at −78° C. for another 30 minutes, the cooling bath is removed and the reaction mixture is stirred for a further one hour. This gives the monochlorophosphine X8.

c) The suspension of the monochlorophosphine X8 prepared as described in b) is added dropwise to the suspension of $(R_C,S_{Fc})$-1-[2-[1-N,N-dimethylaminoethyl]-1-ferrocenyl]cyclohexylphosphino-1'-lithioferrocene prepared as described in a) while stirring, with the temperature being kept below −20° C. The cooling is subsequently removed and the mixture is stirred for 1.5 hours. The reaction mixture is admixed with 5 ml of saturated, aqueous NaHCO$_3$ solution, the organic phase is separated off, dried over Na$_2$SO$_4$ and then evaporated to dryness under reduced pressure. The residue is heated at 150° C. for 1.5 hours. During this treatment, the diastereomer mixture isomerizes preferentially into one diastereomer. Chromatographic purification (SiO$_2$: firstly hexane:EtOAc=3:1, then with an additional 1% of Et$_3$N) gives 5.60 g of product B5 (orange solid, yield: 63%) in the first fraction. The second fraction is a mixture of diastereomers. Renewed thermal treatment with subsequent chromatography finally gives a total of 7.83 g of product B5 (yield: 89%). $^1$H NMR(C$_6$D$_6$, 300 MHz): δ1.00 (dd, J=10.8 and 5.7 Hz, 3H), 1.29 (d, J=6.7 Hz, 6H), 1.66 (dd, J=16.0 and 7.2 Hz, 3H), 0.90~2.41 (m, 10H), 2.25 (s, 12H), 2.66 (m, 1H), 2.90 (m, 1H), 3.96 (br. s, 1H), 3.98 (br. s, 1H), 4.03~4.62 (m, 12H), 4.09 (s, 10H), 4.87 (m, 2H); $^{31}$P NMR(C$_6$D$_6$, 101 MHz): δ −24.0 and −26.5.

EXAMPLE 8

Preparation of [(R$_C$,R$_C$),(S$_{Fc}$,S$_{Fc}$),(S$_P$,S$_P$)]-1-[2-(1-N,N-dimethylamino-ethyl)-1-ferrocenyl](4-methoxyphenyl)phosphino-1'-[2-(1-N,N-dimethylaminoethyl)-1-ferrocenyl]cyclohexylphosphinoferrocene of the formula (B6)

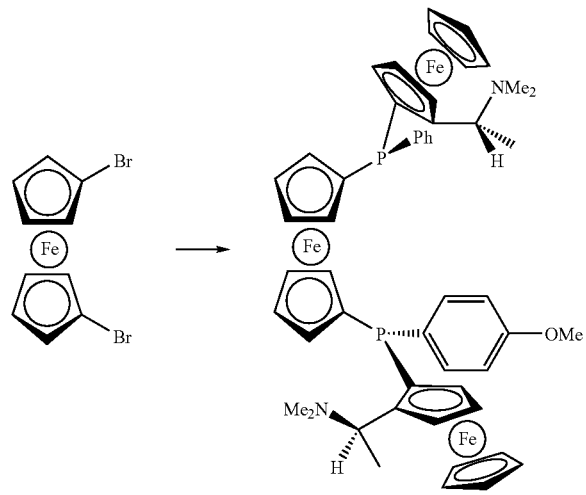

Reaction mixture a): 7.7 ml (10 mmol) of s-BuLi (1.3 M in cyclohexane) are added dropwise to a cooled solution of 2.57 g (10 mmol) of (R)-N,N-dimethyl-1-ferrocenyl-ethylamine [(R)-Ugi amine] in TBME (15 ml) at such a rate that the temperature remains below −20° C. After the addition, the temperature is allowed to rise to 0° C. and the mixture is stirred at this temperature for another 1.5 hours. The mixture is then cooled to −78° C. and 1.52 ml (10 mmol) of cyclohexyldichlorophosphine are added dropwise at such a rate that the temperature does not exceed −60° C. The mixture is stirred at −78° C. for a further 30 minutes, the cooling is then removed and the suspension containing the monochlorophosphine $(R_C,S_{Fc})$-[2-(1-N,N-dimethylamino-ethyl)-1-ferrocenyl]cyclohexylchlorophosphine is stirred for a further 1 hour.

Reaction mixture b): In a second reaction flask, 4.0 ml (10 mmol) of n-BuLi (2.5 M in hexane) are added dropwise to a solution of 3.43 g (10 mmol) of 1,1'-dibromo-ferrocene in 10 ml of THF which has cooled to −30° C. at such a rate that the temperature does not exceed −30° C. The mixture is subsequently stirred at −30° C. for a further 1.5 hours and the mixture containing the 1-bromo-1'-lithioferrocene is finally cooled to −78° C.

Reaction mixture c): The reaction mixture a) is added to the cooled reaction mixture b) at such a rate that the temperature does not exceed −20° C. After the addition, the cooling is removed and the reaction mixture is stirred for a further 1 hour. The mixture is then cooled back down to at least −50° C. and 7.7 ml (10 mmol) of s-BuLi (1.3 M in cyclohexane) are added at such a rate that the temperature does not exceed −30° C. The mixture is subsequently cooled in ice and stirred at 0° C. The reaction mixture containing the $(R_C,S_{Fc})$-1-[2-(1-N,N-dimethylaminoethyl)-1-ferrocenyl]cyclohexyl-phosphine-1'-lithioferrocene is finally cooled to <−50° C.

Reaction mixture d): 7.7 ml (10 mmol) of s-BuLi (1.3 M in cyclohexane) are added dropwise to a cooled solution of (R)-N,N-dimethyl-1-ferrocenylethylamine[(R)-Ugi amine] (2.57 g, 10 mmol) in TBME (15 ml) at such a rate that the temperature remains below −20° C. After the addition, the temperature is allowed to rise to 0° C. and the mixture is stirred at this temperature for a further 1.5 hours. It is then cooled to −78° C. and 2.09 g (10 mmol) of 4-methoxyphenyldichlorophosphine are added dropwise at such a rate that the temperature does not exceed −60° C. The mixture is stirred at −78° C. for a further 30 minutes, the cooling is then removed and the suspension containing the monochlorophosphine $(R_C,S_{Fc})$-[2-(1-N,N-dimethylamino-ethyl)-1-ferrocenyl]-4-methoxyphenylchlorophosphine is stirred for another 1 hour.

The reaction mixture d) is added to the cooled reaction mixture c) at such a rate that the temperature does not exceed −20° C. After the addition, the cooling is removed and the reaction mixture is stirred at room temperature for a further 1.5 hours.

15 ml of saturated NaHCO$_3$ solution are added, the reaction mixture is extracted with ethyl acetate, the organic phases are collected, dried over sodium sulphate and the solvent is distilled off under reduced pressure on a rotary evaporator. The residue is heated at 150° C. for 1.5 hours and subsequently purified by chromatography (silica gel; eluent=ethyl acetate/hexane 1:3). The first fraction gives the product as a yellow-orange solid in a yield of 54%.

$^1$H NMR(C$_6$D$_6$, 300 MHz): δ1.19 (d, J=6.7 Hz, 3H), 1.29 (d, J=6.7 Hz, 3H), 1.85 (s, 6H), 2.26 (s, 6H), 0.98~2.48 (m, 11H), 3.44 (s, 3H), 3.91 (m, 1H), 4.05 (m, 1H), 4.09 (s, 5H), 4.18 (s, 5H), 4.13~4.20 (m, 5H), 4.22 (m, 1H), 4.26 (m, 1H), 4.44 (m, 1H), 4.46 (m, 2H), 4.56 (m, 1H), 4.60 (m, 1H), 4.87 (m, 2H); $^{31}$P NMR(C$_6$D$_6$, 101 MHz): δ −26.5 and −37.4.

EXAMPLE 9

Preparation of [(R$_C$,R$_C$),(S$_{Fc}$,S$_{Fc}$),(S$_P$,S$_P$)]-1-[2-(1-N,N-dimethylamino-ethyl)-1-ferrocenyl](4-trifluoromethylphenyl)phosphino-1'-[2-(1-N,N-dimethylamino-ethyl)-1-ferrocenyl]cyclohexylphosphinoferrocene of the formula (B7)

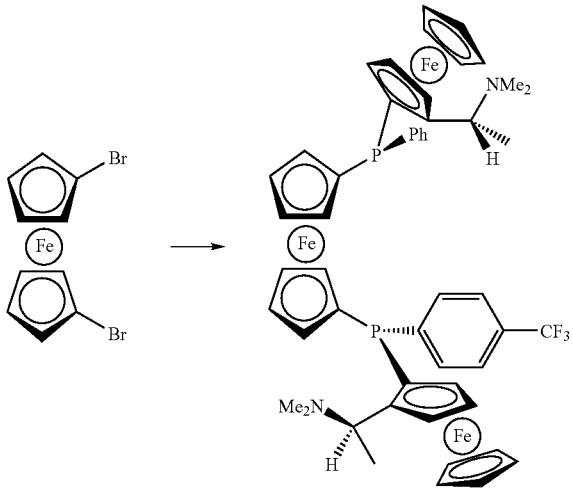

The compound B7 is prepared in a manner analogous to the compound B6 in Example 8, except that 4-trifluoromethylphenyldichlorophoshine is used in place of 4-methoxyphenyldichlorophosphine for the reaction mixture d).

After thermal treatment (heating to 150° C. for 1 hour without solvent), the crude product is purified by chromatography (silica gel; eluent=ethyl acetate/hexane 1:8). The first fraction gives the desired product in a yield of 53%.

$^1$H NMR(C$_6$D$_6$, 300 MHz): δ0.99 (d, J=6.7 Hz, 3H), 1.18 (d, J=6.7 Hz, 3H), 1.54 (s, 6H), 2.11 (s, 6H), 1.04~2.40 (m, 11H), 3.78 (m, 1H), 3.80 (m, 1H), 3.89 (m, 1H), 3.94 (m, 2H), 3.97 (s, 5H), 4.01 (m, 1H), 4.04 (s, 5H), 4.07 (m, 2H), 4.17 (m, 3H), 4.24 (m, 1H), 4.40 (m, 1H), 4.47 (m, 1H), 4.71 (m, 2H), 7.40 (d, J=8.1 Hz, 2H), 7.66 (dd, J=8.1 and 7.3 Hz, 2H); $^{31}$P NMR(C$_6$D$_6$, 101 MHz): δ −26.5 and −34.7.

EXAMPLE 10

Preparation of [(R$_C$,R$_C$),(S$_{Fc}$,S$_{Fc}$),(S$_P$,S$_P$)]-1-[2-(1-N,N-dimethylamino-ethyl)-1-ferrocenyl](4-trifluoromethylphenyl)phosphino-1'-[2-(1-N,N-dimethylamino-ethyl)-1-ferrocenyl](4-methoxyphenyl)phosphinoferrocene of the formula (B8)

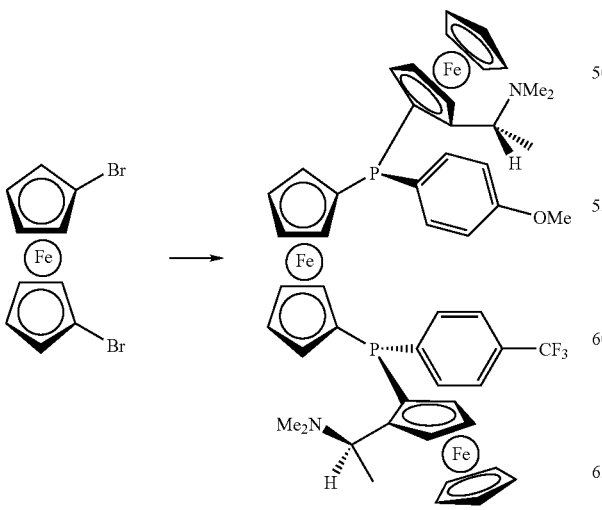

The compound B8 is prepared in a manner analogous to the compound B6 in Example 8, except that 4-methoxyphenyldichlorophosphine is used in place of cyclohexyldichlorophosphine for the reaction mixture a) and 4-trifluoromethylphenyldichlorophoshine is used in place of 4-methoxyphenyldichlorophosphine for the reaction mixture d).

After thermal treatment (heating to 150° C. for 1 hour without solvent), the crude product is purified by chromatography (silica gel; eluent=ethyl acetate/hexane 1:5). The first fraction gives the desired product in a yield of 52%.

$^1$H NMR(C$_6$D$_6$, 300 MHz): δ 0.93 (d, J=6.7 Hz, 3H), 1.01 (d, J=6.7 Hz, 3H), 1.48 (s, 6H), 1.66 (s, 6H), 3.29 (s, 3H), 3.43 (m, 1H), 3.56 (m, 1H), 3.86 (m, 2H), 3.88 (m, 1H), 3.92 (m, 1H), 3.97 (s, 5H), 3.99 (m, 2H), 4.00 (s, 5H), 4.03 (m, 2H), 4.12 (m, 2H), 4.23 (m, 2H), 4.69 (m, 2H), 6.72 (d, J=8.2 Hz, 2H), 7.31 (d, J=8.2 Hz, 2H), 7.50~7.57 (m, 4H); $^{31}$P NMR (C$_6$D$_6$, 101 MHz): δ −34.9 and −37.7.

EXAMPLE 11

Preparation of [(R$_C$,R$_C$),(S$_{Fc}$,S$_{Fc}$),(S$_P$,S$_P$)]-1-[2-(1-N,N-dimethylamino-ethyl)-1-ferrocenyl]phenylphosphino-1'-[2-(1-methoxyethyl)-1-ferrocenyl]phenylphosphinoferrocene of the formula (B9)

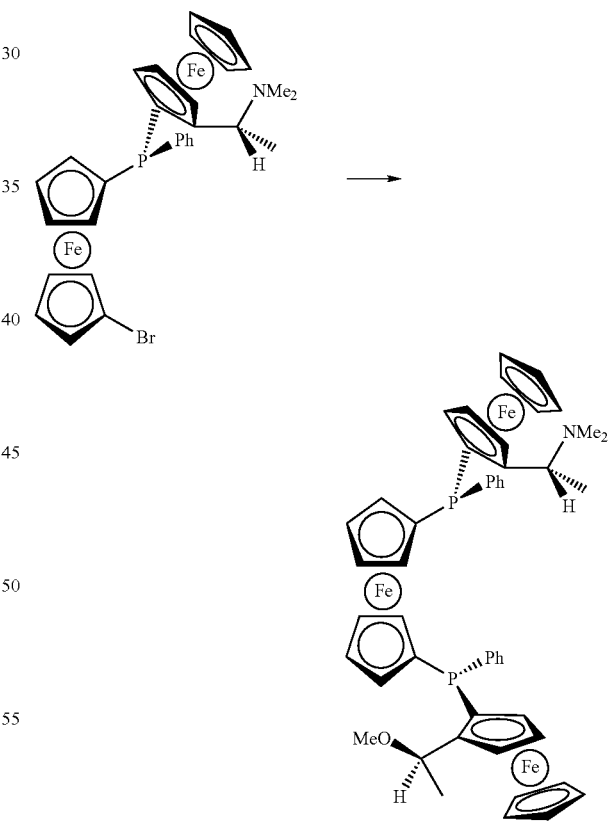

Reaction mixture a): 3.4 ml (5 mmol) of t-BuLi (1.5 M in pentane) are added dropwise to a cooled solution of (R)-1-methoxyethylferrocene 1.22 g (5 mmol) in TBME (5 ml) at such a rate that the temperature remains below −40° C. After the addition, the temperature is allowed to rise to 0° C. and the mixture is stirred at this temperature for another 1.5 hours. The mixture is then cooled to −78° C. and 0.68 ml (5 mmol)

of phenyldichlorophosphine is added dropwise at such a rate that the temperature does not exceed −60° C. The mixture is stirred at −78° C. for a further 30 minutes, the cooling is then removed and the reaction mixture containing the monochlorophosphine ($R_C$,$S_{Fc}$)-[2-(1-methoxyethyl)-1-ferrocenyl] phenylchlorophosphine is stirred for another 1 hour.

Reaction mixture b): In a second reaction flask, 3.85 ml (5 mmol) of sec-BuLi (1.3 M in cyclohexane) are added dropwise to a solution of 3.15 g (5 mmol) of ($R_C$,$S_{Fc}$,$S_P$)-1-[2-(1-N,N-dimethylaminoethyl)-1-ferrocenyl]phenylphosphino-1'-bromoferrocene in 10 ml of TMBE which has been cooled to −78° C. at such a rate that the temperature does not exceed −60° C. The reaction solution containing the lithiated ferrocene is subsequently stirred at −78° C. for another 1 hour.

The reaction mixture b) is added to the reaction mixture a) which has been cooled to −78° C. at such a rate that the temperature does not exceed −60° C. After the addition, the cooling is removed and the reaction mixture is stirred further for 1.5 hours. 10 ml of water are then added and the reaction mixture is extracted with ethyl acetate. The organic phases are collected, dried over sodium sulphate and the solvent is distilled off under reduced pressure on a rotary evaporator. The residue is purified by chromatography (silica gel; eluent=ethyl acetate/hexane 1:5). This gives a mixture of 2 diastereomers (ratio about 1:1). Thermal treatment (1.5 hours at 145° C.) leads to a diastereomers ratio of about 9:1. The main diastereomer is obtained in pure form in a yield of 61% by chromatography (silica gel; eluent=ethyl acetate/hexane 1:5).

$^1$H NMR($C_6D_6$, 300 MHz): δ 1.00 (d, J=6.7 Hz, 3H), 1.40 (d, J=6.7 Hz, 3H), 1.61 (s, 6H), 2.68 (s, 3H), 3.52 (m, 1H), 3.60 (m, 1H), 3.87 (m, 1H), 3.91~3.98 (m, 5H), 4.00 (s, 5H), 4.01 (s, 5H), 4.03 (m, 1H), 4.18 (m, 1H), 4.20 (m, 2H), 4.24 (m, 1H), 4.66 (m, 1H), 4.71 (m, 1H), 4.73 (m, 1H), 6.98~7.11 (m, 6H), 7.61~7.68 (m, 4H). $^{31}$P NMR($C_6D_6$, 101 MHz): δ −35.1 and −35.3.

EXAMPLE 12

Preparation of [($R_C$,$R_C$),($S_{Fc}$,$S_{Fc}$),($S_P$,$S_P$)]-1-[2-(1-N,N-dimethylamino-ethyl)-1-ferrocenyl]phenylphosphino-1'-[2-(α-N,N-dimethylaminophenylmethyl)-1-ferrocenyl]phenylphosphinoferrocene of the formula (B10)

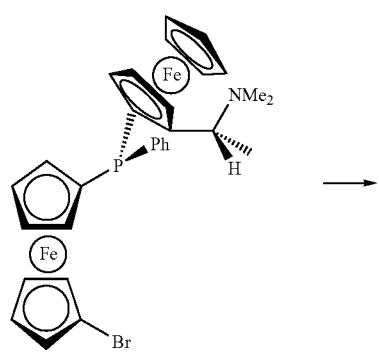

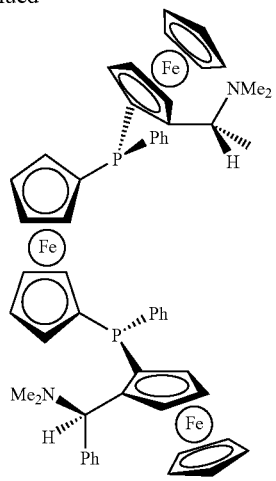

Reaction mixture a): 3.85 ml (5 mmol) of s-BuLi (1.3 M in cyclohexane) are added dropwise to a cooled solution of (R)[α-(N,N-dimethylamino)phenylmethyl]ferrocene 1.60 g (5 mmol) in TBME (5 ml) at such a rate that the temperature remains below −40° C. After the addition, the temperature is allowed to rise to 0° C. and the mixture is stirred at this temperature for another 1.5 hours. The mixture is then cooled to −78° C. and 0.68 ml (5 mmol) of phenyldichlorophosphine is added dropwise at such a rate that the temperature does not exceed −60° C. The mixture is stirred at −78° C. for a further 30 minutes, the cooling is then removed and the reaction mixture containing the monochlorophosphine ($R_C$,$S_{Fc}$)-[2-(α-N,N-dimethylaminophenylmethyl)-1-ferrocenyl]phenylchlorophosphine is stirred for a further 1 hour.

Reaction mixture b): In a second reaction flask, 3.85 ml (5 mmol) of sec-BuLi (1.3 M in cyclohexane) are added dropwise to a solution of 3.15 g (5 mmol) of ($R_C$,$S_{Fc}$,$S_P$)-1-[2-(1-N,N-dimethylaminoethyl)-1-ferrocenyl]phenylphosphino-1'-bromoferrocene in 10 ml of TMBE which has been cooled to −78° C. at such a rate that the temperature does not exceed −60° C. The reaction mixture containing the lithiated ferrocene is subsequently stirred at −78° C. for another 1 hour.

The reaction mixture b) is added to the reaction mixture a) which has been cooled to −78° C. at such a rate that the temperature does not exceed −60° C. After the addition, the cooling is removed and the reaction mixture is stirred for a further 1.5 hours. 10 ml of water are then added and the reaction mixture is extracted with ethyl acetate. The organic phases are collected, dried over sodium sulphate and the solvent is distilled off under reduced pressure on a rotary evaporator. The residue is heated at 150° C. for 1 hour and subsequently purified by chromatography (silica gel; eluent=ethyl acetate/hexane 1:5). The product is obtained in a yield of 43%.

$^1$H NMR (CDCl$_3$, 300 MHz): δ 1.16 (d, J=6.7 Hz, 3H), 1.48 (s, 6H), 1.52 (s, 6H), 3.43 (m, 1H), 3.58 (s, 5H), 3.84 (m, 1H), 3.88 (m, 1H), 3.90 (m, 1H), 3.95 (m, 1H), 4.04 (s, 5H), 4.12 (m, 1H), 4.15 (m, 1H), 4.17 (m, 1H), 4.23 (m, 1H), 4.30 (m, 3H), 4.41 (m, 1H), 4.64 (m, 2H), 7.22~7.63 (m, 15H). 31P NMR (CDCl$_3$, 101 MHz): δ −35.3 and −36.4.

EXAMPLE 13
[($R_C$,$R_C$),($S_{Fc}$,$S_{Fc}$), ($S_P$,$S_P$)]-1,1'-Bis[2-(1-N,N-dimethylaminoethyl)-1-ferrocenyl]cyclohexylphosphinoferrocene of the formula (B11) [R=cyclohexyl; Me=methyl]
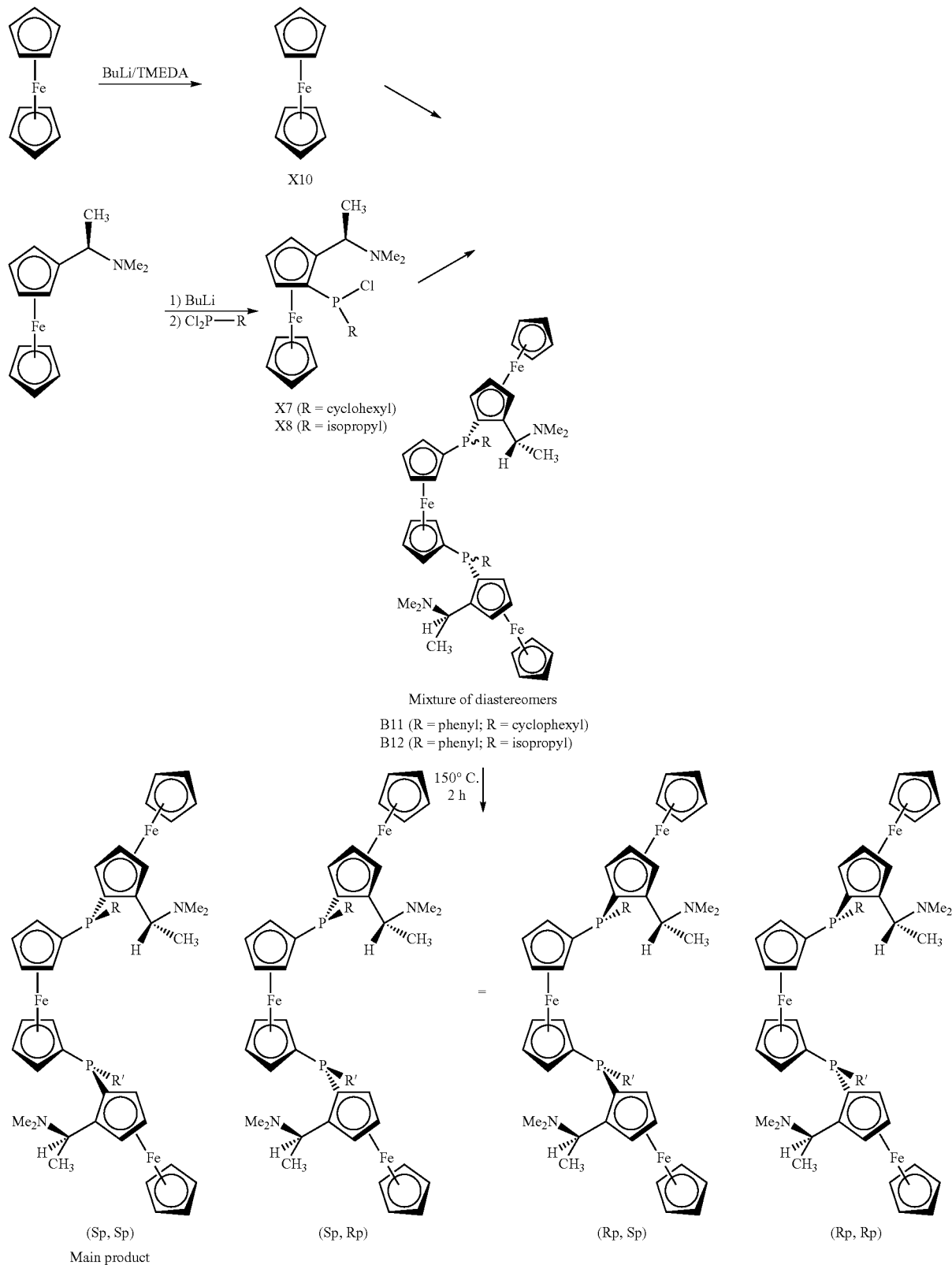
B11 (R = phenyl; R = cyclohexyl)
B12 (R = phenyl; R = isopropyl)
(Sp, Sp) Main product    (Sp, Rp)    (Rp, Sp)    (Rp, Rp)

a) 13.7 ml (22 mmol, 1.6 M in hexane) of n-BuLi are added to a suspension of 1.86 g of ferrocene (10 mmol) and 3.20 ml of TMDEA (20 mmol) in 20 ml of hexane over a period of 10 minutes. Stirring is continued at 50° C. for another 2 hours and the reaction mixture containing the dilithioferrocene X10 is then used in the next step.

b) 15.4 ml of a cyclohexane solution of s-BuLi (1.3 M, 22 mmol) are added to a solution of 5.14 g (20 mmol) of (R)-N,N-dimethyl-1-ferrocenylethylamine[(R)-Ugi amine] in 30 ml of t-butyl methyl ether (TBME) at <20° C. over a period of 10 minutes. The mixture is then heated to 0° C. while stirring and maintained at this temperature for 1.5 hours. It is then cooled to <60° C. and 3.0 ml (20 mmol) of dichlorocyclohexyl-phosphine are added over a period of 10 minutes. After stirring the mixture at −78° C. for 30 minutes, it is allowed to warm slowly to room temperature and is stirred at this temperature for 1.5 hours.

c) The suspension prepared as described in a) is added to the reaction mixture prepared as described in b) at below −20° C. The mixture is stirred at room temperature for 2.5 hours and 20 ml of water are then added. The organic phase is separated off, dried over sodium sulphate and the solvent is subsequently removed until the mixture is dry. This gives the product B4 as an orange solid as a mixture of the 3 diastereomers $(S_P,S_p)$, $(S_P,R_P)$ and $(R_P,R_P)$ in a ratio of 1:4:6. The ratio is determined by means of $^{31}$P NMR. $^{31}$P NMR (CDCl$_3$, 101 MHz): $(R_P,R_P)$ isomer: δ −21.6 (s), $(S_P,R_P)$ isomer: δ −21.3 (s) and −26.9 (s); $(S_P,S_P)$ isomer: δ −26.5 (s).

d) The solid obtained as described in c) is maintained at 150° C. for 2 hours. The ratio of $(S_P,S_P):(S_P,R_P):(R_P,R_P)$ is then 2.5:1:0. The mixture of diastereomers is then separated by chromatography (SiO$_2$, firstly hexane:EtOAc=3:1, then hexane:EtOAc=3:1 containing 1% of Et$_3$N). A first fraction containing 5.43 g (58.7% of theory) of the pure title compound B4 is obtained. $^1$H NMR (CDCl$_3$, 300 MHz): δ 1.30 (d, 6H, J=6.6 Hz), 1.28~2.40 (m, 18H), 2.26 (s, 12H), 2.68 (m, 2H), 3.99 (m, 2H), 4.09 (s, 12H, overlapping), 4.21 (m, 2H); 4.30 (m, 2H); 4.53 (m, 2H); 4.56 (m, 2H); 4.63 (m, 2H); 4.86 (m, 2H) ppm. $^{31}$P NMR (CDCl$_3$, 101 MHz): δ −26.5 (s). The second fraction contains a mixture of the diastereomers $(S_P,S_p)$ and $(S_P,R_P)$ (2.96 g, 32.0% of theory). Renewed thermal treatment and subsequent chromatographic separation enables the yield of the desired diastereomer to be increased.

EXAMPLE 14

Preparation of [(R$_C$,R$_C$),(S$_{Fc}$, S$_{Fc}$),(S$_P$,S$_P$)]-1,1'-bis[2-(1-N,N-dimethyl-aminoethyl)-1-ferrocenyl]isopropylphosphinoferrocene of the formula (B12) [R=iso-propyl; Me=methyl]

a) 13.7 ml (22 mmol, 1.6 M in hexane) of n-BuLi are added to a suspension of 1.86 g of ferrocene (10 mmol) and 3.20 ml of TMDEA (20 mmol) in 20 ml of hexane over a period of 10 minutes. Stirring is continued at 50° C. for 2 hours and the reaction mixture containing the dilithioferrocene X10 is then used in the next step.

b) 15.4 ml of a cyclohexane solution of s-BuLi (1.3 M, 22 mmol) are added to a solution of 5.14 g (20 mmol) of (R)-N,N-dimethyl-1-ferrocenylethylamine[(R)-Ugi amine] in 30 ml of t-butyl methyl ether (TBME) at <20° C. over a period of 10 minutes. The mixture is then warmed to 0° C. while stirring and maintained at this temperature for 1.5 hours. It is then cooled to <60° C. and 2.47 ml (20 mmol) of dichloroisopropylphosphine are added over a period of 10 minutes. After stirring at −78° C. for 30 minutes, the mixture is allowed to warm slowly to room temperature and is stirred at this temperature for 1.5 hours.

c) The suspension prepared as described in a) is added to the reaction mixture prepared as described in b) at below −20° C. The mixture is stirred at room temperature for 2.5 hours and 20 ml of water are then added. The organic phase is then separated off, dried over sodium sulphate and the solvent is subsequently removed until the mixture is dry. The product B5 is obtained as an orange solid comprising a mixture of the 3 diastereomers $(S_P,S_P)$, $(S_P,R_P)$ and $(R_P,R_P)$ in a ratio of 1:4.8:7.7. The ratio is determined by means of $^{31}$P NMR. $^{31}$P NMR (CDCl$_3$, 101 MHz): $(R_P,R_P)$ isomer: δ −16.4 (s), $(S_P,R_P)$ isomer: δ −18.8 (s) and −24.1 (s); $(S_P,S_P)$ isomer: δ −23.8 (s).

d) The solid obtained as described in c) is maintained at 150° C. for 2 hours. The ratio of $(S_P,S_P):(S_P,R_P):(R_P,R_P)$ is then 14:7:1. A chromatographic separation (SiO$_2$, firstly hexane:EtOAc=3:1, then hexane:EtOAc=3:1 containing 1% of Et$_3$N) is then carried out. This gives a first fraction containing 4.85 g (57.5% of theory) of the pure title compound B5. $^1$H NMR (CDCl$_3$, 300 MHz): δ 1.25 (m, 12H, overlapping), 1.68 (dd, 6H, J=18.5 and 7.3 Hz), 2.25 (s, 12H); 2.85 (m, 2H), 3.96 (m, 2H); 4.10 (s, 12H, overlapping), 4.21 (m, 2H); 4.26 (m, 2H); 4.47 (m, 2H); 4.55 (m, 4H); 4.89 (m, 2H) ppm. $^{31}$P NMR (CDCl$_3$, 101 MHz): δ −23.8 (s). The second fraction contains a mixture of the 3 diastereomers $(S_p,S_p)$, $(S_P,R_P)$ and $(R_P,R_P)$ (2.20 g, 32.0% of theory). Renewed thermal treatment and the subsequent chromatographic separation enables the yield of the desired diastereomer to be increased.

C) Preparation of Metal Complexes

EXAMPLE C1

Preparation of a Rhodium Complex (nbd is norbornadiene)

11.6 mg (0.0131 mmol) of ligand B3 and 4.9 mg (0.0131 mmol) of [Rh(nbd)$_2$]BF$_4$ are dissolved in 0.8 ml of CD$_3$OD/CH$_2$Cl$_2$ 1:1 and the solution is stirred for 10 minutes.

The solution is then transferred to an NMR tube for measurement. $^{31}$P NMR (121.5 MHz, CD$_3$OD): two doublets. Possible assignment: δ 11.5 (d, J$_{Rh-p}$=172 Hz), 8.3 (d, J$_{Rh-P}$=170 Hz).

D) Use Examples (Hydrogenations)

EXAMPLES D1 TO D7

Hydrogenation of

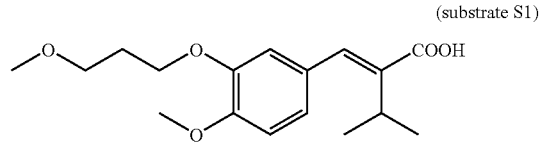

(substrate S1)

All manipulations are carried out under argon using degassed solvents.

2.17 mg (0.00238 mmol) of ligand B1 and 0.85 mg (0.00227 mmol) of [Rh(nbd)$_2$]BF$_4$ are weighed into a 25 ml Schlenk vessel provided with a magnetic stirrer and rubber septum and dissolved in 8 ml of methanol. The solution is stirred for about 10 minutes and a solution of 8.4 g (27.24 mmol) of substrate S1 in 27 ml of methanol is then added. 1.7 mg of trifluoroacetic acid are then added. The resulting solution is transferred under pressure via a cannula into a 50 ml steel autoclave which has previously been filled with argon. The autoclave is connected via a reducing valve to a hydrogen reservoir. The autoclave is closed, placed in a heating bath at the desired temperature and the argon is replaced by hydrogen by pressurizing with hydrogen and depressurizing twice. The autoclave is then pressurized with hydrogen to the desired pressure and the hydrogenation is started by switching on the stirrer. After the hydrogenation, the stirrer is switched off, the autoclave is depressurized and the hydrogenation solution is taken out. The conversion and the enantiomeric excess (ee) are determined by means of HPLC (Chirapak AD; 0.46×250 mm; hexane/ethanol (EtOH)/acetic acid (AcOH) 950:50:1; flow=0.7 ml/minute; 20° C.

An analogous procedure is employed for the ligands B2 to B5 and the comparative ligand C1.

The comparative ligand C1 is [($R_C,R_C$,)($S_{Fc},S_{Fc}$,)($S_P,S_P$)-1-[2-(1-dimethylaminoethyl)-ferrocenyl]phenylphosphino-1'-[2-(1-dimethylaminoethyl)ferrocenyl]cyclohexylphosphinoferrocene (see WO 2006/075166, Example 1).

*Examples D6-D7 and Comparison* are carried out in a manner analogous to Examples D1-D5, except that 6 g of substrate S1 in 17 ml of methanol are used and no trifluoroacetic acid is added.

The results are in shown Table 1.

TABLE 1

| Examples | Ligand | S/Cat. | Temp. [° C.] | Pressure [bar] | React. time [h] | Conversion | ee | Configuration |
| --- | --- | --- | --- | --- | --- | --- | --- | --- |
| Comparison | C1 | 12000 | 35 | 50 | 3.5 | 13.9 | 99.5 | S |
| Comparison | C1 | 12000 | 50 | 50 | 20 | 92.0 | 96.8 | S |
| Comparison* | C1 | 8500 | 35 | 60 | 20.5 | 20.4 | 96.2 | S |
| D1 | B1 | 12000 | 35 | 50 | 3.5 | 44.0 | 99.6 | S |
| D2 | B2 | 12000 | 35 | 50 | 3.5 | 51.0 | 99.0 | S |
| D3 | B5 | 12000 | 35 | 50 | 3.5 | 82.9 | 96.8 | S |
| D4 | B11 | 12000 | 35 | 50 | 3.5 | 81.2 | 99.6 | S |
| D5 | B11 | 12000 | 50 | 50 | 3.5 | 100 | 99.2 | S |
| D6 | B12 | 8500 | 35 | 60 | 20.5 | 98.3 | 96.2 | S |
| D7 | B1 | 8500 | 35 | 60 | 20.5 | 100 | 99.5 | S |

EXAMPLES D8-D10

Hydrogenation of

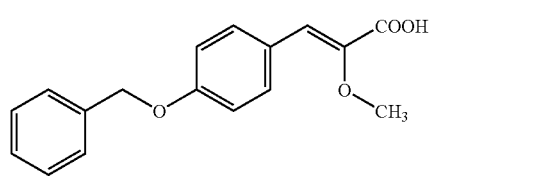

(substrate S2)

All manipulations are carried out under argon using degassed solvents. 0.94 mg (0.0025 mmol) of [Rh(nbd)$_2$]BF$_4$ and 0.00275 mmol of the ligand (see Table 2) are weighed into a 25 ml Schlenk vessel provided with a magnetic stirrer and rubber septum. After addition of 1 ml of methanol, the mixture is stirred for 20 minutes. A solution of 143 mg (0.5 mmol) of the substrate S2 in 4 ml of methanol is added to the catalyst solution obtained. The resulting solution is transferred under pressure via a cannula to a 50 ml steel autoclave provided with a glass liner and magnetic stirrer. The hydrogenation is then carried under in a manner analogously to Examples D1-D7. The conversion and the enantiomeric excess (ee) are determined by means of HPLC (Chirapak AD-H). The results are summarized in Table 2.

TABLE 2

| Example | Ligand | S/Cat. | Temp. [° C.] | Pressure [bar] | React. time [h] | Conversion | ee |
| --- | --- | --- | --- | --- | --- | --- | --- |
| D8 | B1 | 200 | 40 | 20 | 17 | 100 | 98.3 |
| D9 | B2 | 200 | 40 | 20 | 17 | 100 | 97.6 |
| D10 | B11 | 200 | 40 | 20 | 17 | 100 | 97.2 |

EXAMPLES D11 TO D13

Hydrogenation of Various Substrates

The hydrogenations are carried out in 1.2 ml ampoules. Instead of stirring, the ampoules are shaken vigorously. In a glove box, solutions which have a volume of about 0.5 ml and whose composition can be taken from Table 1 are prepared in the 1.2 ml ampoules under a nitrogen atmosphere. The catalysts are prepared in situ by mixing 1 equivalent of the metal precursor with 1.3 equivalents of ligand in dichloro-ethane and subsequently distilling off the dichloroethane under reduced pressure. The substrate is dissolved in the hydrogenation solvent and added as solution to the catalyst. The ampoules are fixed in a pressure-rated, heatable container, the container is closed, the desired temperature is set, the nitrogen atmosphere in the container is replaced by a hydrogen atmosphere having the desired pressure and the hydrogenation is started by switching on the shaker.

Substrates:

| | Hydrogenation and conditions | Determination of conversion and ee by means of: |
|---|---|---|
| ACA | 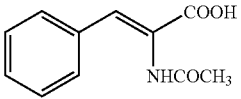 Hydrogenation conditions: 1 bar of $H_2$; 25° C.; 2 h | Firstly derivatization with TMS-diazomethane, then GC using chiral column: Chirasil-L-val |
| MAA | 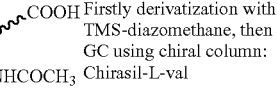 Hydrogenation conditions: 1 bar of $H_2$; 25° C.; 2 h | GC using chiral column: Chirasil-L-val |
| MCA | 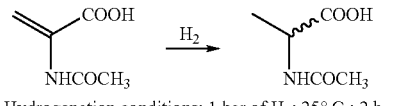 Hydrogenation conditions: 3 bar of $H_2$; 25° C.; 2 h | SFC using chiral column: Chiracel OJH |
| ETPY | 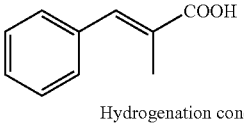 Hydrogenation conditions: 20 bar of $H_2$; 25° C.: 14 h | GC using chiral column: Lipodex E |
| MPG | 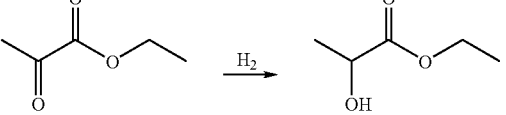 Hydrogenation conditions: 20 bar of $H_2$; 25° C.: 14 h | HPLC using chiral column: Chiracel OD-H |

The results are summarized in Table 3.

TABLE 3

| Example No. | Substrate | Ligand | Cat.[1] | Metal[2] | Solvent | Conversion | ee |
|---|---|---|---|---|---|---|---|
| Comparison | ACA | C1 | 25 | Rh+ | THF | 20 | 94 |
| Comparison | ACA | C1 | 25 | Rh+ | Ethanol | 80 | 91 |
|  | ACA | B1 | 25 | Rh+ | THF | 100 | 97 |
| D11 | ACA | B2 | 25 | Rh+ | THF | 100 | 98 |
|  | ACA | B5 | 25 | Rh+ | Ethanol | 100 | 95 |
|  | ACA | B6 | 25 | Rh+ | Ethanol | 100 | 96 |
|  | ACA | B7 | 25 | Rh+ | Ethanol | 100 | 98 |
|  | ACA | B11 | 25 | Rh+ | THF | 100 | 98 |
| Comparison | ETPY | C1 | 25 | Rh+ | Ethanol | 5 | 1 |
|  | ETPY | B1 | 25 | Rh+ | EtOH | 100 | 72 |
| D12 | ETPY | B2 | 25 | Rh+ | Ethanol | 100 | 64 |
|  | ETPY | B7 | 25 | Rh+ | Ethanol | 100 | 74 |
| Comparison | MPG | C1 | 25 | Rh+ | Ethanol | 20 | 12 |
| D13 | MPG | B2 | 25 | Rh+ | Ethanol | 100 | 82 |
|  | MCA | B4 | 25 | Rh+ | Methanol | 100 | 91 |
|  | MCA | B6 | 25 | Rh+ | Methanol | 100 | 87 |
|  | MCA | B10 | 100 | Rh+ | Methanol | 100 | 90 |
|  | MAA | B9 | 25 | Rh+ | Ethanol | 100 | 90 |

[1] Molar ratio of substrate to catalyst
[2] metal precursor: Rh+ = [Rh(nbd)$_2$]BF$_4$

The invention claimed is:

1. A compounds of the formula I in the form of racemates, an enantiomerically pure diastereomer or a mixture of diastereomers,

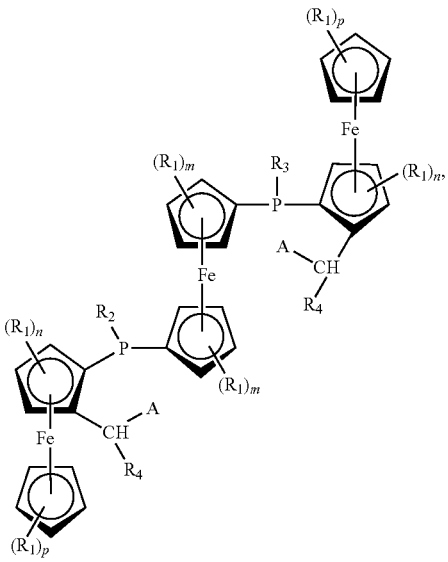

(I)

where
the radicals $R_1$ are identical or different and are each $C_1$-$C_4$-alkyl;
m is 0 or an integer from 1 to 4;
n is 0 or an integer from 1 to 3;

p is 0 or an integer from 1 to 5;
$R_2$ is an aromatic hydrocarbon radical or a C-bonded aromatic heterohydrocarbon radical and $R_3$ is an aliphatic or C-bonded heteroaliphatic hydrocarbon radical; or
$R_2$ and $R_3$ are identical or different and are each an aliphatic or C-bonded heteroaliphatic hydrocarbon radical;
$R_4$ is an unsubstituted or $C_1$-$C_6$-alkyl-, $C_1$-$C_6$-alkoxy- or halogen-substituted hydrocarbon radical; and
A is a secondary amino group.

2. The compounds according to claim 1, wherein an alkyl group $R_1$ is methyl.

3. The compounds according to claim 1, wherein m and n are each, independently of one another, 1 or 0 and p is 5 or 0.

4. The compounds according to claim 1, wherein the hydrocarbon radicals $R_2$ and $R_3$ are unsubstituted or substituted and/or contain heteroatoms selected from the group consisting of O, S, —N═, —NH— or N($C_1$-$C_4$-alkyl); the aliphatic radicals contain from 1 to 22 carbon atoms and from 0 to 4 of the heteroatoms mentioned; the aromatic radicals contain from 3 to 22 carbon atoms; and the heteroaromatic radicals contain from 3 to 22 carbon atoms and from 1 to 4 of the heteroatoms mentioned.

5. The compounds according to claim 1, wherein an aromatic radical $R_2$ is a radical selected from the group consisting of $C_6$-$C_{14}$-aryl and $C_4$-$C_{12}$-heteroaryl which are unsubstituted or substituted by halogen, $C_1$-$C_6$-alkyl, trifluoromethyl, $C_1$-$C_6$-alkoxy, trifluoromethoxy, $(C_6H_5)_3Si$, $(C_1$-$C_{12}$-alkyl$)_3Si$ or sec-amino and in the case of heteroaryl contains heteroatoms selected from the group consisting of O, S, —N($C_1$-$C_4$-alkyl)- and —N═.

6. The compound according to claim 5, wherein $R_2$ is o-furyl, phenyl, naphthyl, 2-($C_1$-$C_6$-alkyl)$C_6H_4$, 3-($C_1$-$C_6$-alkyl)$C_6H_4$, 4-($C_1$-$C_6$-alkyl)$C_6H_4$, 2-($C_1$-$C_6$-alkoxy)$C_6H_4$, 3-($C_1$-$C_6$-alkoxy)$C_6H_4$, 4-($C_1$-$C_6$-alkoxy)$C_6H_4$, 2-(trifluoromethyl)$C_6H_4$, 3-(trifluoromethyl)$C_6H_4$, 4-(trifluoromethyl)$C_6H_4$, 3,5-bis(trifluoromethyl)$C_6H_3$, 3,5-bis($C_1$-$C_6$-alkyl)$_2C_6H_3$, 3,5-bis($C_1$-$C_6$-alkoxy)$_2C_6H_3$ or 3,5-bis($C_1$-$C_6$-alkyl)$_2$-4-($C_1$-$C_6$-alkoxy)$C_6H_2$.

7. The compounds according to claim 1, wherein an aliphatic or C-bonded heteroaliphatic hydrocarbon radical $R_2$ is a radical selected from the group consisting of linear or branched $C_1$-$C_{12}$-alkyl; linear or branched $C_2$-$C_{12}$-heteroalkyl; unsubstituted or $C_1$-$C_6$-alkyl- or $C_1$-$C_6$-alkoxy-substituted $C_4$-$C_{12}$-cycloalkyl or $C_4$-$C_{12}$-cycloalkyl-$CH_2$—; unsubstituted or $C_1$-$C_6$-alkyl- or $C_1$-$C_6$-alkoxy-substituted $C_3$-$C_{12}$-heterocycloalkyl or $C_3$-$C_{12}$-heterocycloalkyl-$CH_2$—; $C_7$-$C_{14}$-aralkyl; and $C_4$-$C_{12}$-heteroaralkyl; with heteroatoms being selected from the group consisting of O, S, —NH— and —N($C_1$-$C_4$-alkyl)-.

8. The compounds according to claim 1, wherein $R_2$ and $R_3$ are each, independently of one another, $C_1$-$C_6$-alkyl, $C_5$-$C_8$-cycloalkyl, $C_5$-$C_8$-cycloalkylmethyl or $C_7$-$C_{10}$-polycycloalkyl.

9. The compounds according to claim 1, wherein $R_2$ is o-furyl, phenyl, naphthyl, 2-($C_1$-$C_6$-alkyl)$C_6$-$C_4$, 3-($C_1$-$C_6$-alkyl)$C_6H_4$, 4-($C_1$-$C_6$-alkyl)$C_6H_4$, 2-($C_1$-$C_6$-alkoxy)$C_6H_4$, 3-($C_1$-$C_6$-alkoxy)$C_6H_4$, 4-($C_1$-$C_6$-alkoxy)$C_6H_4$, 2-(trifluoromethyl)$C_6H_4$, 3-(trifluoromethyl)$C_6H_4$, 4-(trifluoromethyl)$C_6H_4$, 3,5-bis(trifluoromethyl)$C_6H_3$, 3,5-bis($C_1$-$C_6$-alkyl)$_2C_6H_3$, 3,5-bis($C_1$-$C_6$-alkoxy)$_2C_6H_3$ and 3,5-bis($C_1$-$C_6$-alkyl)$_2$-4-($C_1$-$C_6$-alkoxy)$C_6H_2$ and $R_3$ $C_1$-$C_6$-alkyl, $C_5$-$C_8$-cycloalkyl, $C_5$-$C_8$-cycloalkylmethyl or $C_7$-$C_{10}$-polycycloalkyl.

10. The compounds according to claim 1, wherein $R_4$ is a radical selected from the group consisting of linear or branched $C_1$-$C_8$-alkyl; unsubstituted or halogen (F, Cl or Br)—, $C_1$-$C_6$-alkyl- or $C_1$-$C_6$-alkoxy-substituted $C_4$-$C_8$-cycloalkyl or $C_4$-$C_8$-cycloalkyl-$CH_2$—; unsubstituted or halogen (F, Cl or Br)—, $C_1$-$C_6$-alkyl- or $C_1$-$C_6$-alkoxy-substituted $C_6$-$C_{14}$-aryl or $C_7$-$C_{14}$-aralkyl.

11. The compounds according to claim 10, wherein $R_4$ is $C_1$-$C_4$-alkyl, $C_5$-$C_6$-cycloalkyl, phenyl, $C_1$-$C_4$-alkylphenyl or $C_1$-$C_4$-alkylbenzyl.

12. The compounds according to claim 10, wherein $R_4$ is methyl.

13. The compounds according to claim 1, wherein the secondary amino group corresponds to the formula —$NR_5R_6$, where $R_5$ and $R_6$ are identical or different and are each $C_1$-$C_8$-alkyl, $C_5$-$C_8$-cycloalkyl, phenyl or benzyl or $R_5$ and $R_6$ together with the N atom form a five- to eight-membered ring.

14. The compounds according to claim 13, wherein $R_5$ and $R_6$ are identical radicals and are each $C_1$-$C_4$-alkyl or together are tetramethylene, pentamethylene or 3-oxa-1,5-pentylene.

15. The compounds according to claim 1, wherein the group —$CHR_4$-A is 1-dimethylaminoeth-1-yl or 1-(dimethylamino)-1-phenylmethyl.

16. A complex of metal selected from the group of transition metals with a compound of the formula I as defined in claim 1 as ligand.

17. The metal complex according to claim 16, wherein the transition metal is selected from the group consisting of Cu, Ag, Au, Fe, Ni, Co, Rh, Pd, Ir, Ru and Pt.

18. A process for preparing a chiral organic compound by asymmetric addition of hydrogen onto a carbon-carbon or carbon-heteroatom double bond in a prochiral organic compound in the presence of a catalyst, wherein the addition is carried out in the presence of a catalytic amount of at least one metal complex according to claim 16.

19. The process according to claim 18, wherein the organic compound corresponds to the formula VI,

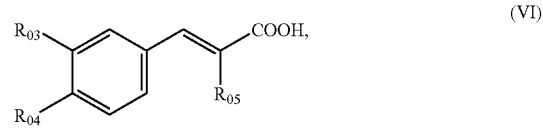

(VI)

where
$R_{03}$ and $R_{04}$ are each, independently of one another, H, $C_1$-$C_6$-alkyl, $C_1$-$C_6$-haloalkyl, $C_1$-$C_6$-alkoxy, $C_1$-$C_6$-alkoxy-$C_1$-$C_6$-alkyl or $C_1$-$C_6$-alkoxy-$C_1$-$C_6$-alkyloxy and $R_{05}$ is $C_1$-$C_6$-alkyl, and is hydrogenated by means of hydrogen in the presence of a rhodium complex with a ligand of the formula I as metal complex and catalyst to give a compound of the formula VII

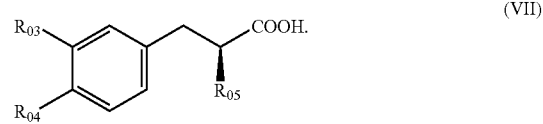

(VII)

20. The compounds according to claim 2, wherein m and n are each, independently of one another, 1 or 0 and p is 5 or 0.

21. A method for asymmetric addition of hydrogen onto a carbon-carbon or carbon-heteroatom double bond in a prochiral organic compound for preparing a chiral organic compound, which comprises carrying out the addition in the presence of 0.0001 to 10 mol %, based on the compound be to hydrogenated, of the metal complex according to claim 16 as a homogenous catalyst.

* * * * *